United States Patent
Yamamoto

(10) Patent No.: US 10,470,746 B2
(45) Date of Patent: Nov. 12, 2019

(54) ULTRASOUND DIAGNOSTIC APPARATUS, SOUND VELOCITY DETERMINING METHOD, AND RECORDING MEDIUM

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 652 days.

(21) Appl. No.: 14/670,608

(22) Filed: Mar. 27, 2015

(65) Prior Publication Data

US 2015/0196284 A1 Jul. 16, 2015

Related U.S. Application Data

(63) Continuation of application No. PCT/JP2013/075676, filed on Sep. 24, 2013.

(30) Foreign Application Priority Data

Sep. 28, 2012 (JP) ................. 2012-217090

(51) Int. Cl.
*A61B 8/00* (2006.01)
*G10K 11/34* (2006.01)
(Continued)

(52) U.S. Cl.
CPC .......... *A61B 8/5269* (2013.01); *A61B 8/4488* (2013.01); *A61B 8/485* (2013.01);
(Continued)

(58) Field of Classification Search
CPC ... A61B 8/5261; A61B 8/4245; A61B 8/0825; A61B 8/4416; A61B 8/485; A61B 8/58;
(Continued)

(56) References Cited

U.S. PATENT DOCUMENTS 5,570,691 A * 11/1996 Wright ................ G01S 7/52049
600/447
8,226,561 B2 * 7/2012 McLaughlin .......... G01N 29/14
600/443
(Continued)

FOREIGN PATENT DOCUMENTS

| JP | 1997224938 A | * | 9/1997 | ............... A61B 8/00 |
| JP | 2009078124 A | * | 4/2009 | ............... A61B 8/00 |
| JP | 2011-092686 A |   | 5/2011 | |

OTHER PUBLICATIONS

English translation of the International Preliminary Report on Patentability and Written Opinion of the International Searching Authority (Forms PCT/IB/338, PCT/IB/373 and PCT/ISA/237), dated Apr. 9, 2015, for International Application No. PCT/JP2013/075676.

(Continued)

*Primary Examiner* — Baisakhi Roy
*Assistant Examiner* — Patrick M Mehl
(74) *Attorney, Agent, or Firm* — Birch, Stewart, Kolasch & Birch, LLP

(57) ABSTRACT

In the ultrasound diagnosis, a probe performs transmission of an ultrasonic beam a plurality of times so as to form predetermined transmission focus points, the analog reception data output by the probe is A/D converted to turn into a first element data, a plurality of first element data is used to generate a second element data corresponding to any one of the plurality of first element data, and a sound velocity is determined using the first element data in a case where the position for determining the sound velocity is in a vicinity of the transmission focus point and using the second element data in a case where the position is not in a vicinity of the transmission focus point. In this manner, the sound velocity (Continued)

of the ultrasound waves in an inspection object can be accurately determined without decreasing the frame rate.

18 Claims, 9 Drawing Sheets

(51) Int. Cl.
    *A61B 8/08*     (2006.01)
    *G01S 7/52*     (2006.01)
    *G01S 15/89*     (2006.01)
    *A61B 8/14*     (2006.01)

(52) U.S. Cl.
    CPC ........ *A61B 8/5207* (2013.01); *G01S 7/52049* (2013.01); *G01S 15/8904* (2013.01); *G01S 15/8915* (2013.01); *G10K 11/346* (2013.01); *A61B 8/0858* (2013.01); *A61B 8/14* (2013.01)

(58) Field of Classification Search
    CPC .... A61B 8/08; A61B 8/00; A61B 8/14; G01S 7/52049; G01S 15/8915; G01S 15/8904; G10K 11/346; G10K 11/345
    See application file for complete search history.

(56) References Cited

U.S. PATENT DOCUMENTS

| | | | |
|---|---|---|---|
| 2010/0036251 A1* | 2/2010 | Baba ................... | G10K 11/346 600/447 |
| 2011/0077518 A1* | 3/2011 | Miyachi ............ | A61B 5/02007 600/443 |
| 2011/0077519 A1 | 3/2011 | Katsuyama | |
| 2013/0296706 A1 | 11/2013 | Katsuyama | |
| 2013/0303912 A1 | 11/2013 | Katsuyama | |

OTHER PUBLICATIONS

International Search Report issued in PCT/JP2013/075676, dated Dec. 24, 2013.

\* cited by examiner

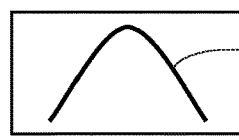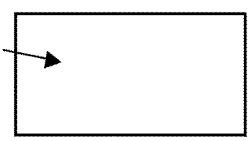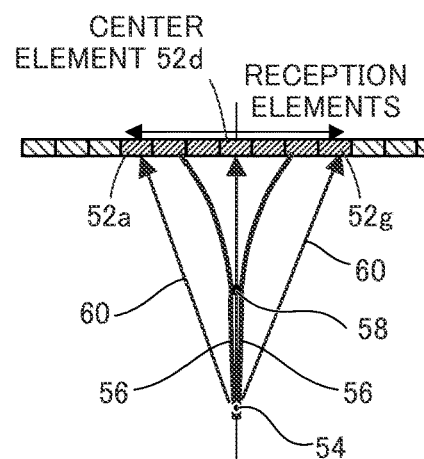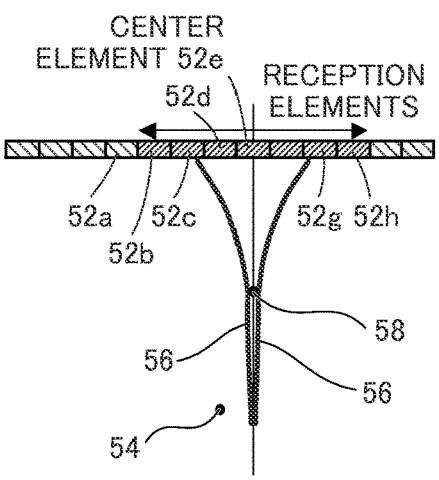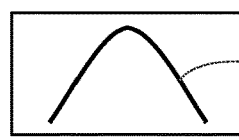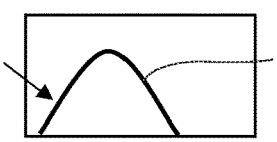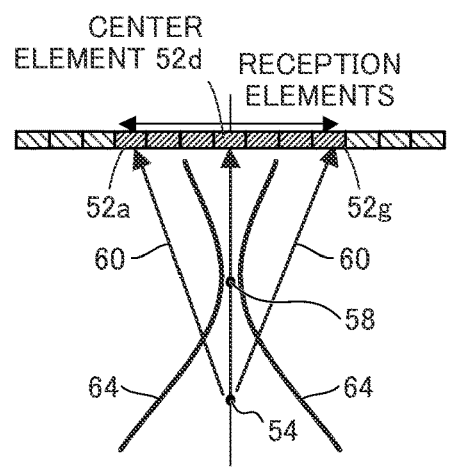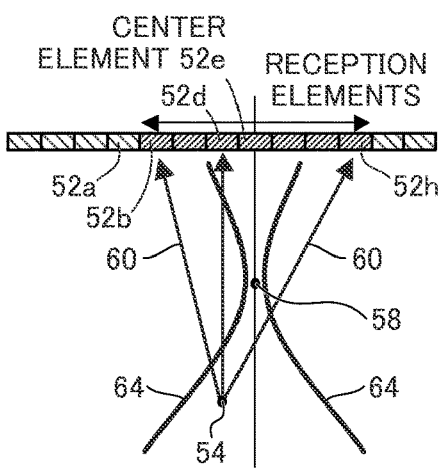

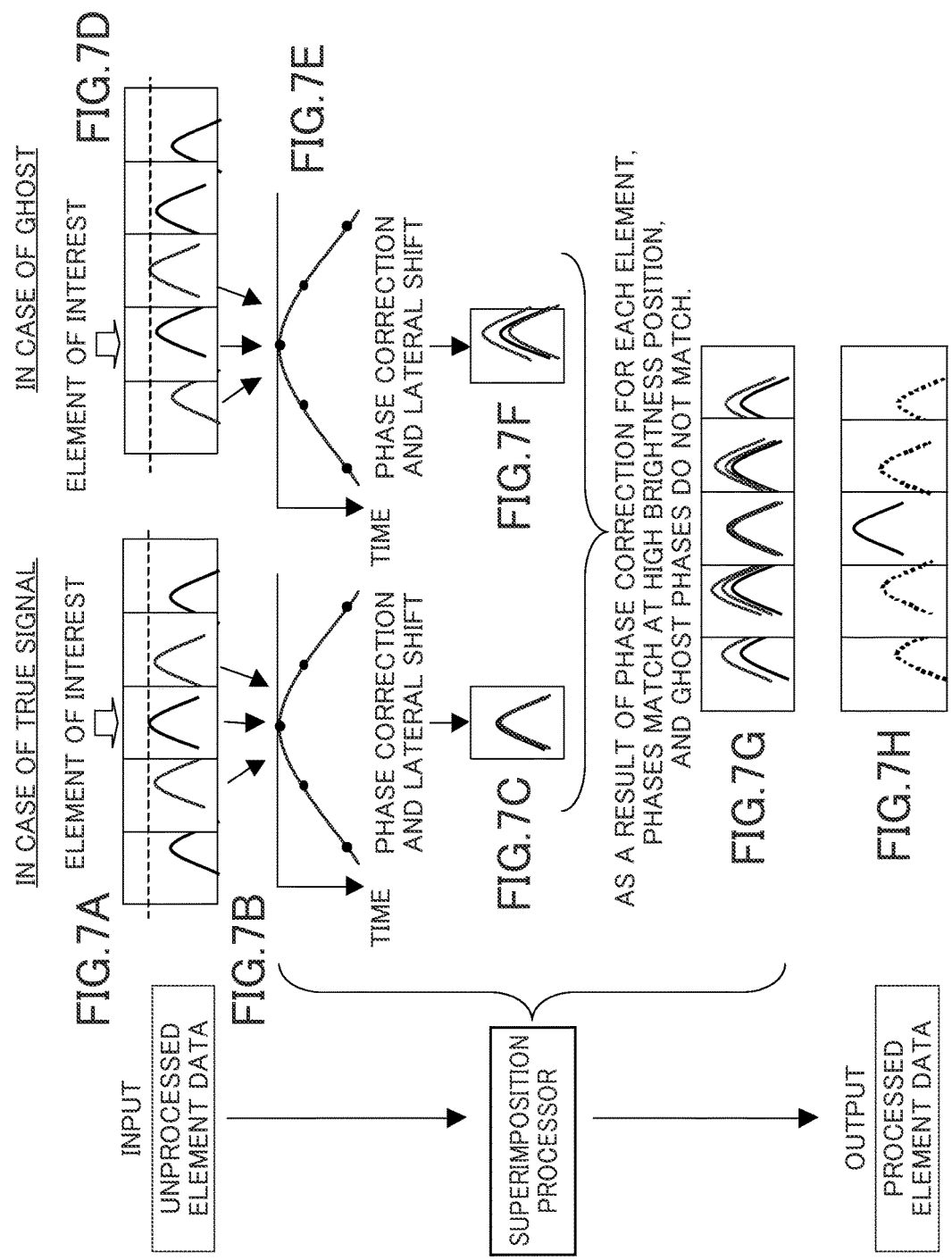

ULTRASOUND DIAGNOSTIC APPARATUS, SOUND VELOCITY DETERMINING METHOD, AND RECORDING MEDIUM

CROSS-REFERENCE TO RELATED APPLICATIONS

This application is a Continuation of PCT International Application No. PCT/JP2013/075676 filed on Sep. 24, 2013, which claims priority under 35 U.S.C. § 119(a) to Japanese Application No. 2012-217090 filed on Sep. 28, 2012. The above application(s) is hereby expressly incorporated by reference, in its entirety, into the present application.

BACKGROUND OF THE INVENTION

The present invention relates to an ultrasound diagnostic apparatus having a function of determining a sound velocity inside an inspection object, a method of determining a sound velocity inside an inspection object, and a recording medium in which a program determining a sound velocity of an inspection object in an ultrasound diagnosis is recorded.

Conventionally, ultrasound diagnostic apparatuses such as ultrasound image diagnostic apparatuses using ultrasound images are put to practical use in the medical field.

Generally, this type of ultrasound diagnostic apparatus has an ultrasound probe (hereinafter, referred to as "probe") with a plurality of built-in elements (ultrasound transducers) and an apparatus main body connected with the probe. In the ultrasound diagnostic apparatus, an ultrasonic beam is transmitted toward a subject (an inspection object) so as to form a predetermined focus point (transmission focus) from the plurality of elements of the probe, an ultrasonic echo from the subject is received in the probe, and an ultrasound image is generated by electrically processing the reception signal of the received ultrasonic echo in the apparatus main body.

Here, in the ultrasound diagnostic apparatus, an ultrasonic echo from a subject according to a single transmission of the ultrasonic beam is received by a plurality of elements. Accordingly, even with ultrasonic echoes reflected by the same reflector, the reception time of the ultrasonic echoes is delayed according to the position of each of the elements.

Therefore, in the ultrasound diagnostic apparatus, an ultrasound image is generated by analog-to-digital (A/D) converting the reception signal of the ultrasonic echoes received in each of the elements into a digital reception signal (hereinafter, referred to as element data), and then carrying out a reception focusing process on the element data. That is, in the ultrasound diagnostic apparatus, reception data (sound ray signals) is generated by performing delay correction on the element data according to a delay time, matching the phases, and performing phasing addition, and an ultrasound image is generated using the reception data.

In conventional ultrasound diagnostic apparatuses, the sound velocity of ultrasonic waves in the subject is assumed to be constant, and the reception focusing process was performed by fixing a sound velocity of the ultrasonic waves to a predetermined certain value.

However, the sound velocity varies depending on the type of tissues such as fatty layers, muscular layers in a living body, and therefore the sound velocity of ultrasonic waves is not uniform in the subject. In addition, the thicknesses of fatty layers and muscular layers are different in fat subject and slim subject. In other words, the sound velocity of ultrasonic waves varies from person to person.

Accordingly, in a conventional ultrasound diagnostic apparatus in which the sound velocity of ultrasonic waves is fixed, when the actual sound velocity in a subject differs from a set sound velocity, the arrival time for the ultrasonic echoes to be reflected inside the subject and reach the elements does not match with a set delay time.

As a result, there is a problem in that proper phase matching is not possible, reception focusing is not properly performed, and the image quality of the obtained ultrasound image deteriorates. In addition, there is also a problem in that the obtained ultrasound image is distorted with respect to the actual subject.

With respect to such problems, in the ultrasound diagnostic apparatus, the sound velocity in the subject is determined (calculated), and the reception focusing process is performed using this sound velocity.

For example, JP 2011-92686 A describes an ultrasound diagnostic apparatus which transmission and reception of ultrasonic waves after setting a region of concern where a diagnosis region in a subject is divided in an ultrasound image to be photographed, calculates a focus index for each of a plurality of sound velocities (set sound velocities) set in advance in each region of concern by performing a reception focusing process with respect to obtained element data using a plurality of sound velocities (set sound velocities) set as appropriate, and uses the calculated focus indexes to determine the sound velocity (the ambient sound velocity) in each region of concern.

Examples of the focus indexes include contrast, brightness, and the like. For example, a set sound velocity where the brightness set as the focus index was the highest may be determined as the sound velocity in the region of concern.

SUMMARY OF THE INVENTION

In the ultrasound diagnostic apparatus described in JP 2011-92686 A, an ultrasound image is generated by performing a reception focusing process by correcting or selecting a delay time or delay pattern according to the determined sound velocity. Due to this, regardless of the differences in the sound velocities depending on the location in the subject or among the subjects, it is possible to stably output a proper ultrasound image.

Here, with this method, it is possible to determine an accurate sound velocity in a location where a wavefront shape of ultrasonic echoes (reflected waves) is clear. However, it is often not possible to determine an accurate sound velocity at positions separated from a focus, or the like.

Therefore, depending on the position in the subject (the ultrasound image), there are cases where it is not possible to perform a proper reception focusing process even when using the determined sound velocity and an ultrasound image with a high image quality cannot be obtained.

On the other hand, in order to determine an accurate sound velocity corresponding to every location in the subject, transmission (transmission and reception) of ultrasonic waves may be performed corresponding to a large number of focus points where the positions in the depth and azimuth direction are different.

However, when the transmission and reception of ultrasonic waves is performed corresponding to a large number of focus points, there is another problem in that the frame rate of the ultrasound image decreases in accordance with the updating or the like of the sound velocities.

An object of the present invention is to solve the problems of the prior art techniques and to provide an ultrasound diagnostic apparatus, a sound velocity determining method, and a program which are able to accurately determine a sound velocity in all locations in an inspection object in an ultrasound diagnosis even without performing transmission and reception of ultrasonic waves corresponding to a large number of focus points in the depth direction.

In order to attain the above-described object, an ultrasound diagnostic apparatus according to the present invention, which inspects an inspection object using an ultrasonic beam, comprises:

a probe in which a plurality of elements are arranged, which transmit the ultrasonic beam, receive ultrasonic echoes reflected by the inspection object, and output an analog element signal according to the received ultrasonic echoes;

a transmitter configured to make the probe perform transmission of the ultrasonic beam a plurality of times so as to form predetermined transmission focus points using the plurality of elements;

a receiver configured to receive an analog element signal output by the plurality of elements corresponding to the transmission of the ultrasonic beam toward each of the transmission focus points, and carrying out a predetermined process;

an analog-to-digital converter configured to analog-to-digital convert the analog element signal processed by the receiver into first element data which is a digital element signal;

a data processor configured to generate second element data corresponding to any one of a plurality of first element data;

a sound velocity determiner configured to determine a sound velocity of ultrasonic waves in the inspection object using the first element data or the second element data; and a position determiner configured to determine whether or not a position at which the sound velocity determiner determines the sound velocity is in a vicinity of a position of one of the transmission focus points, wherein the sound velocity determiner determines the sound velocity using the first element data in a case where the sound velocity determining position is in a vicinity of the one of the transmission focus points according to determination results by the position determiner and determines the sound velocity using the second element data in a case where the sound velocity determining position is not in the vicinity of the one of the transmission focus points.

In the ultrasound diagnostic apparatus according to the present invention, preferably, the transmitter makes the probe perform transmission of the ultrasonic beam a plurality of times, changing at least one of a center element and a transmission direction of the ultrasonic beam.

Preferably, the data processor generates the second element data using at least one of a plurality of the first element data obtained by transmission of the ultrasonic beam where the center elements are different to each other and a plurality of the first element data obtained by transmission of the ultrasonic beam where the transmission directions are different to each other.

Preferably, the data processor generates the second element data from the plurality of first element data obtained by transmission of the ultrasonic beam where transmission regions overlap.

Preferably, the data processor generates the second element data by superimposing the plurality of first element data according to a reception time at which the elements received the ultrasonic echoes and positions of the elements.

Preferably, a measurement region in a subject is divided into a plurality of regions and the sound velocity is determined for each divided region.

Preferably, the transmitter performs the transmission of the ultrasonic beam for one sound ray at only one of the transmission focus points when determining the sound velocity.

Preferably, the ultrasound diagnostic apparatus further comprises: an element data storage unit which stores all of the first element data corresponding to at least one ultrasound image.

Preferably, an ultrasound image is formed using the second element data.

Preferably, the ultrasound image is formed by performing phasing addition for forming the ultrasound image using the sound velocity determined by the sound velocity determiner.

In addition, the present invention provides a sound velocity determining method in ultrasound diagnosis using a probe in which a plurality of elements are arranged, which transmit an ultrasonic beam, receive ultrasonic echoes reflected by an inspection object, and output an analog element signal according to the received ultrasonic echoes, the method comprising:

making the probe perform transmission of the ultrasonic beam a plurality of times so as to form predetermined transmission focus points using the plurality of elements when determining a sound velocity of the ultrasonic waves inside an inspection object;

analog-to-digital converting an analog element signal output by the plurality of elements into first element data which is a digital element signal corresponding to the individual transmission of the ultrasonic beam corresponding to each of the transmission focus points;

generating, using a plurality of first element data, second element data corresponding to any one of the plurality of first element data;

determining whether or not a position for determining the sound velocity of the ultrasonic waves in the inspection object is in a vicinity of one of the transmission focus points; determining the sound velocity using the first element data in a case where the position for determining the sound velocity is in a vicinity of one of the transmission focus points; and determining the sound velocity using the second element data in a case where the position for determining the sound velocity is not in the vicinity of one of the transmission focus points.

In the sound velocity determining method according to the present invention, preferably, the probe performs transmission of the ultrasonic beam a plurality of times, changing at least one of a center element and a transmission direction of the ultrasonic beam.

Preferably, the second element data is generated using either one of or both of the plurality of first element data obtained by transmission of the ultrasonic beam where the center elements are different to each other and the plurality of first element data obtained by transmission of the ultrasonic beam where the transmission directions are different to each other.

Preferably, the second element data is generated from the plurality of first element data obtained by transmission of the ultrasonic beam where transmission regions overlap.

Preferably, the second element data is generated by superimposing the plurality of first element data according to a reception time at which the elements received the ultrasonic echoes and positions of the elements.

Preferably, a measurement region in a subject is divided into a plurality of regions and the sound velocity is determined for each divided region.

Preferably, the transmission of the ultrasonic beam for one sound ray is performed at only one of the transmission focus points.

Furthermore, the present invention provides a non-transitory computer-readable recording medium which records a program making a computer execute the steps of: making a probe in which a plurality of elements are arranged, which transmit the ultrasonic beam, receive ultrasonic echoes reflected by an inspection object, and output an analog element signal according to the received ultrasonic echoes, perform transmission of an ultrasonic beam a plurality of times so as to form predetermined transmission focus points using the plurality of elements;

analog-to-digital converting an analog element signal output by the elements into first element data which is a digital element signal corresponding to the individual transmission of the ultrasonic beam;

generating, using a plurality of first element data, second element data corresponding to any one of the plurality of first element data;

determining whether or not a position for determining the sound velocity in the inspection object is in a vicinity of one of the transmission focus points; and determining the sound velocity using the first element data in a case where the position for determining the sound velocity is in the vicinity of one of the transmission focus points, and determining the sound velocity using the second element data in a case where the position for determining the sound velocity is not in the vicinity of one of the transmission focus points.

In the program recorded in the non-transitory recording medium according to the present invention, preferably, in the step of making a probe transmit the ultrasonic beam, the probe perform transmission of the ultrasonic beam a plurality of times, changing at least one of a center element and a transmission direction of the ultrasonic beam.

Preferably, in the step of generating the second element data, the second element data is generated using either one of or both of a plurality of first element data obtained by transmission of the ultrasonic beam where center elements are different to each other and a plurality of first element data obtained by transmission of the ultrasonic beam where transmission directions are different to each other.

Preferably, in the step of generating the second element data, the second element data is generated from a plurality of first element data obtained by transmission of the ultrasonic beam where transmission regions overlap.

Preferably, in the step of generating the second element data, the second element data is generated by superimposing a plurality of first element data according to a reception time at which the elements received the ultrasonic echoes and positions of the elements.

According to the present invention, it is possible to accurately determine the sound velocity in all locations in an inspection object in an ultrasound diagnosis even without performing transmission and reception of ultrasonic waves corresponding to a large number of focus points in the depth direction.

Therefore, according to the present invention, it is possible to generate an ultrasound image with high image quality on which a proper reception focusing process is performed using an accurate sound velocity without decreasing the frame rate.

BRIEF DESCRIPTION OF THE DRAWINGS

FIG. 4A and FIG. 4C are each conceptual diagrams for describing transmission and reception of ultrasonic waves using an ideal ultrasonic beam and FIG. 4B and FIG. 4D are each conceptual diagrams showing element data obtained by the transmission and reception of ultrasonic waves.

FIG. 5A and FIG. 5C are each conceptual diagrams for describing the ultrasound transmission and reception according to an actual ultrasonic beam and FIG. 5B and FIG. 5D are each conceptual diagrams showing element data obtained by the transmission and reception of ultrasonic waves.

FIGS. 7A to 7C and FIGS. 7D to 7F are conceptual diagrams for describing element data of a true signal and ghost element data respectively, the delay times thereof, and states where the element data are superimposed, FIG. 7G is a conceptual diagram for describing states where element data corresponding to a plurality of elements are superimposed, and FIG. 7H is a conceptual diagram for describing the results of superimposing the element data in FIG. 7G.

DETAILED DESCRIPTION OF THE INVENTION

Below, detailed description will be given of the ultrasound diagnostic apparatus, the sound velocity determining method, and the recording medium of the present invention based on suitable embodiments illustrated in the accompanying drawings.

Figure 1:
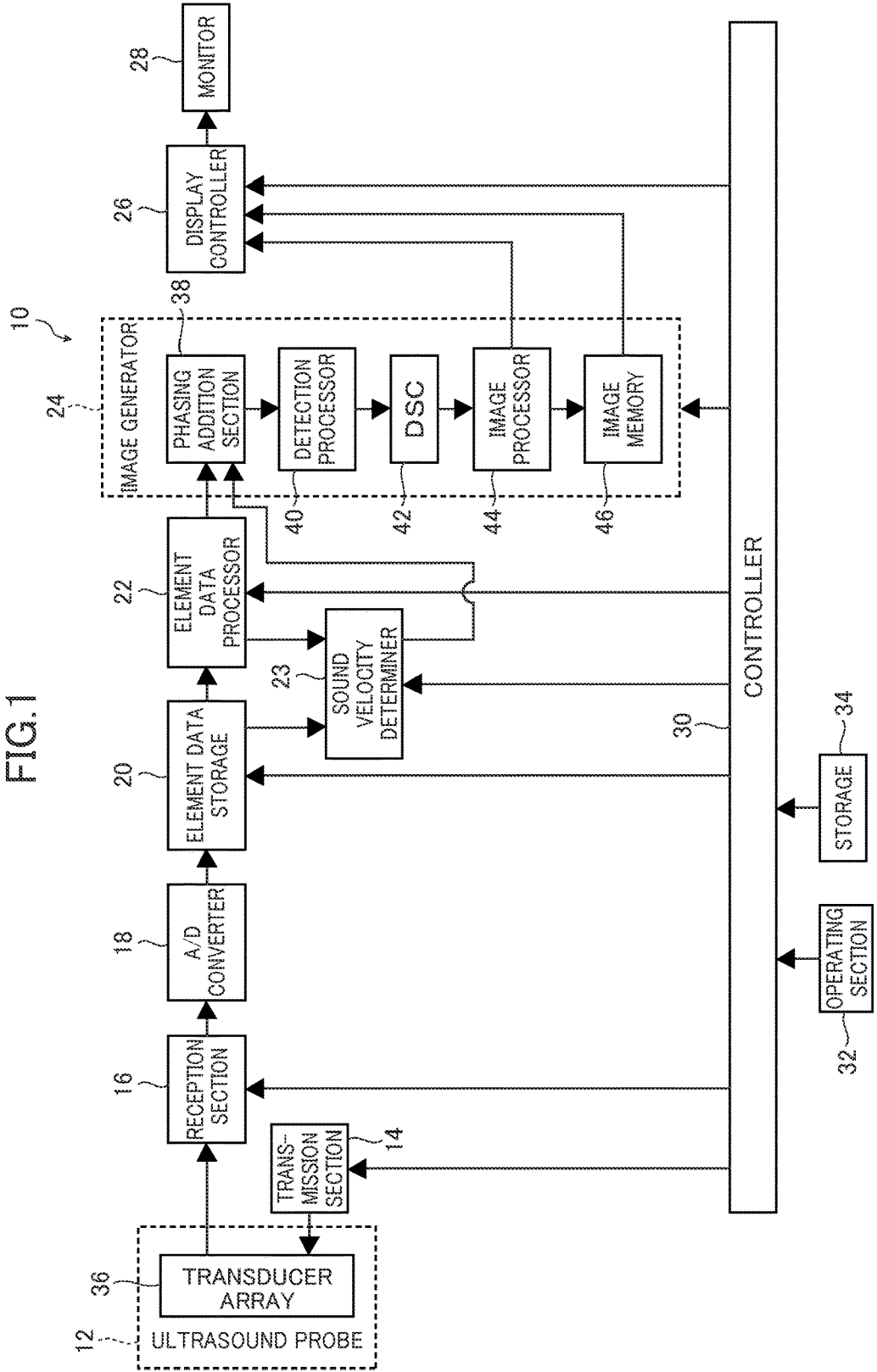
FIG. 1 is a block diagram conceptually illustrating an example of a configuration of an ultrasound diagnostic apparatus of the present invention.

FIG. 1 is a block diagram conceptually illustrating an example of an ultrasound diagnostic apparatus of the present invention which implements a sound velocity determining method of the present invention.

As illustrated in FIG. 1, an ultrasound diagnostic apparatus 10 has an ultrasound probe 12, a transmission section 14 and a reception section 16 connected with the ultrasound probe 12, an analog-to-digital (A/D) converter 18, an element data storage 20, an element data processor 22, a sound velocity determiner 23, an image generator 24, a display controller 26, a monitor 28, a controller 30, an operating section 32, and a storage 34.

In the example in the diagram, the transmission section 14, the reception section 16, the A/D converter 18, the element data storage 20, the element data processor 22, the sound velocity determiner 23, the image generator 24, the display controller 26, the monitor 28, the controller 30, the operating section 32, and the storage 34 configure the apparatus main body of the ultrasound diagnostic apparatus 10.

The ultrasound probe 12 is a known ultrasound probe used in a normal ultrasound diagnostic apparatus.

The ultrasound probe 12 (hereinafter, referred to as the probe 12) has a transducer array 36 in which ultrasound transducers are one-dimensionally or two-dimensionally arranged.

When taking an ultrasound image of an inspection object (hereinafter, referred to as a subject), the ultrasound transducers each transmit ultrasonic beams to the subject in accordance with a driving signal supplied from the transmission section 14, receive ultrasonic echoes reflected by the subject, and output a reception signal according to the strength of the received ultrasonic waves.

Each ultrasound transducer is configured by an oscillator where electrodes are formed at both ends of a piezoelectric body formed of, for example, a piezoelectric ceramic represented by lead zirconate titanate (PZT), a polymer piezoelectric element represented by polyvinylidene fluoride (PVDF), a piezoelectric single crystal represented by lead magnesium niobate-lead titanate (PMN-PT) solid solution, or the like.

When a pulsed or continuous wave voltage is applied to the electrodes of the oscillator, the piezoelectric body expands and contracts according to the applied voltage, and pulsed or continuous ultrasonic waves are generated from each oscillator. In addition, the ultrasonic waves generated from each of the oscillators converge to be combined (that is, transmission focusing is performed on the ultrasonic waves) at set focus points according to a driving delay of each of the oscillators, thereby forming an ultrasonic beam.

In addition, the oscillators expand and contract due to ultrasonic echoes reflected inside the subject being incident thereto and electric signals are generated according to the size of the expansion and contraction. The electric signals are output to the reception section 16 as the reception signal.

The transmission section 14 has, for example, a plurality of pulsars and supplies a driving signal (applies a driving voltage) to each of the ultrasound transducers (oscillators) of the probe 12.

Based on a transmission delay pattern selected by the controller 30, the transmission section 14 performs transmission focusing for adjusting a delay amount (an application timing of a driving voltage) of a driving signal so as to transmit a desired ultrasonic beam to converge ultrasonic waves transmitted by a predetermined number of ultrasound transducers at set focus points, and supplies the driving signal to the ultrasound transducers. In the example shown in FIGS. 4A to 4C to be described below, transmission focusing is performed such that ultrasonic waves transmitted by three ultrasound transducers converge at set focus points, and the driving signal is supplied to the ultrasound transducers. Here, the transmission delay pattern may be corrected according to an ambient sound velocity to be described below.

The desired ultrasonic beam is transmitted from the probe 12 (the transducer array 36) to the subject in this manner.

According to a control signal from the controller 30, the reception section 16 receives reception signals output by a predetermined number (seven in the example shown in FIGS. 4A and 4C to be described below) of ultrasound transducers corresponding to a single ultrasonic beam transmission, and supplies the result to the A/D converter 18 after carrying out a predetermined process such as amplification.

Here, the method of transmitting and receiving the ultrasonic waves in the ultrasound diagnostic apparatus 10 of the present invention is basically the same as for a known ultrasound diagnostic apparatus.

Accordingly, in a single set of transmission and reception of ultrasonic waves, neither the number of ultrasound transducers which generate the ultrasonic waves nor the number of ultrasound transducers which receive the ultrasonic waves is limited as long as there is more than one of each. Here, the single set of transmission and reception of ultrasonic waves is the transmission of one ultrasonic beam and the reception of ultrasonic echoes corresponding to this transmission. In addition, the number of ultrasound transducers which generate the ultrasonic waves is the number of transmission openings. Furthermore, the number of ultrasound transducers which receive the ultrasonic waves is the number of reception openings.

In addition, in a single transmission and reception, the number of openings may be the same or different in the transmission and the reception.

Furthermore, with ultrasonic beams adjacent in at least the azimuth direction (the arrangement direction of the ultrasound transducers), when transmission regions overlap, neither the number of times (number of sound rays) of the transmission and reception of the ultrasonic waves for forming one ultrasound image nor the intervals, that is, the density of the scanning lines/sound rays, of the ultrasound transducers (center elements) in the center of the transmission and reception is limited. Accordingly, the transmission and reception of the ultrasonic waves may be performed with all of the ultrasound transducers corresponding to the region scanned with ultrasonic waves as the center elements, or the transmission and reception of the ultrasonic waves may be performed with ultrasound transducers at predetermined intervals, such as every two transducers or every four transducers, as the center elements.

The A/D converter 18 A/D converts the analog reception signal supplied from the reception section 16 into element data (first element data) which is a digital reception signal.

The A/D converter 18 supplies the A/D converted element data to the element data storage 20.

The element data storage 20 sequentially stores the element data supplied from the A/D converter 18. In addition, the element data storage 20 stores information (for example, the depth of the reflection position of the ultrasonic waves, the density of the scanning lines, or a parameter indicating a visual field width) relating to the frame rate input from the controller 30 in association with each of the element data.

Preferably, the element data storage 20 stores all of the element data corresponding to at least one ultrasound image (an ultrasound image of one frame) and does not erase the element data of the ultrasound image before display or during display at least until the display of the ultrasound image is finished.

The element data processor 22 generates processed element data (second element data) corresponding to each of the element data by superimposing the element data.

Specifically, under the control of the controller 30, the element data processor 22 superimposes the element data out of the element data stored in the element data storage 20 and obtained by a predetermined number (a plurality) of ultrasonic beam transmissions for which the ultrasound transducers in the center, i.e., the elements in the center (center elements), are different and the transmission regions of the ultrasonic beams overlap, according to the time at which each of the ultrasound transducers receives the ultrasonic echoes and the positions of the ultrasound transducers, thereby generating processed element data corresponding to the element data (element data of an element of interest to be described below).

The element data processor 22 sends the generated processed element data to the sound velocity determiner 23 and the image generator 24.

The sound velocity determiner 23 determines the sound velocity (the ambient sound velocity) of ultrasonic waves in a subject using the element data or the processed element data generated by the element data processor 22.

Detailed description will be given below of the element data processor 22, the processed element data, the sound velocity determiner 23, and the ambient sound velocity.

The image generator 24 generates reception data (sound ray signal) from the processed element data supplied from the element data processor 22 under the control of the controller 30 and generates an ultrasound image from this reception data.

The image generator 24 has a phasing addition section 38, a detection processor 40, a DSC 42, an image processor 44, and an image memory 46.

The phasing addition section 38 performs a reception focusing process by carrying out matching addition on the processed element data generated by the element data processor 22, and generates reception data.

As described above, in the transducer array 36 of the probe 12, a plurality of elements (ultrasound transducers) is one-dimensionally or two-dimensionally arranged. Accordingly, the distance to one reflection point in the subject is different for each of the ultrasound transducers. Therefore, even with ultrasonic echoes reflected at the same reflection point, the time for the ultrasonic echoes to arrive at each of the ultrasound transducers is different. According to a reception delay pattern selected by the controller 30, the phasing addition section 38 delays each of the processed element data by an amount corresponding to the difference (the delay time) in the arrival time of the ultrasonic echoes for each of the ultrasound transducers, and carries out matching addition on the processed element data to which the delay time is added, thereby digitally performing a reception focusing process and generating reception data.

The phasing addition section 38 supplies the generated reception data to the detection processor 40.

Here, in a case where the sound velocity (the ambient sound velocity) of the ultrasonic waves in the subject is determined by the sound velocity determiner 23 and supplied to the phasing addition section 38, the phasing addition section 38 performs the reception focusing process by correcting the delay time, the reception delay pattern, or the like using the ambient sound velocity.

Here, in a case where the ambient sound velocity is not determined, the phasing addition section 38 performs the reception focusing process with a known method in which a reception delay pattern is used.

Figure 2:
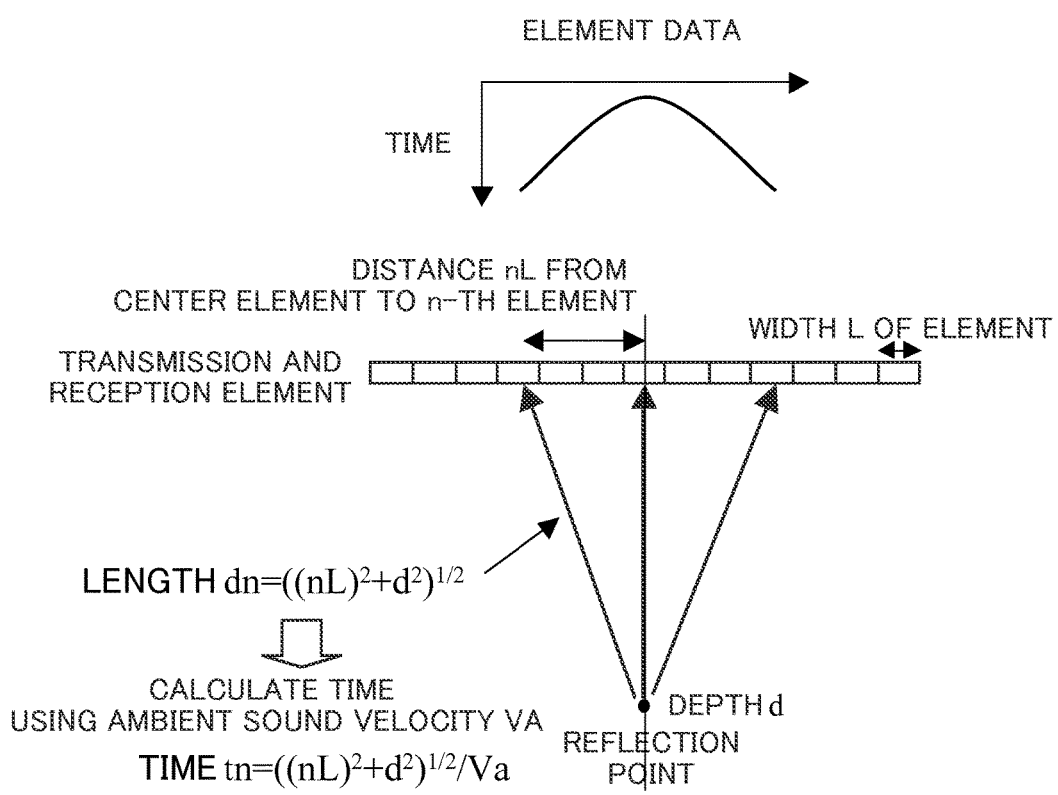
FIG. 2 is a conceptual diagram for describing an example of a reception focusing process in the ultrasound diagnostic apparatus depicted in FIG. 1.

FIG. 2 shows an example of the reception focusing process using the ambient sound velocity.

Here, FIG. 2 shows a case of a linear probe where the plurality of ultrasound transducers of the probe 12 is arranged in a row in the left and right direction in the diagram. However, the concept may be similarly applied even in the case of a convex probe where only the probe shape is different.

When the width of each of the ultrasound transducers (elements) in the azimuth direction is taken to be L, the distance up to the n-th ultrasound transducer from the ultrasound transducer in the center of the azimuth direction toward the end section is nL.

As shown in the same diagram, when the reflection point of the ultrasonic waves is taken to be at a position at a distance (depth) d, which is perpendicular to the arrangement direction, from the center ultrasound transducer, the distance (length) dn between the n-th ultrasound transducer and the reflection point is calculated using the formula (1).

$$dn = ((nL)^2 + d^2)^{1/2} \tag{1}$$

Accordingly, using the ambient sound velocity Va, a time tn for the ultrasonic echoes from the reflection point to arrive at (be received by) the n-th ultrasound transducer is calculated using the formula (2).

$$tn = dn/Va = ((nL)^2 + d^2)^{1/2}/Va \tag{2}$$

As described above, the distance between the ultrasound transducers and the reflection point is different for each ultrasound transducer. Therefore, in the case of this example, as shown in the graph at the top of the same diagram, the arrival time tn of the ultrasonic echoes is longer for the ultrasound transducers toward the end section sides in the arrangement direction.

Specifically, when the time until the ultrasonic waves are received by the center ultrasound transducer from the reflection point is taken to be t1, the ultrasonic waves received by the n-th ultrasound transducer are delayed by the time $\Delta t = tn - t1$ with respect to the ultrasonic waves received by the center ultrasound transducer. In the present example, the delay time $\Delta t$ is a reception delay pattern.

The phasing addition section 38 performs phasing addition for the reception data corresponding to each of the ultrasound transducers using the delay time represented by the time $\Delta t$ described above and performs a reception focusing process.

Here, in the present invention, the reception focusing process according to the ambient sound velocity is not limited to this method and it is possible to use various known methods.

For example, the controller 30 may select a reception delay pattern according to the ambient sound velocity and supply the control signal according thereto to the phasing addition section 38. Alternatively, the controller 30 may correct the reception delay pattern according to the ambient sound velocity and supply the control signal according to the corrected reception delay pattern to the phasing addition section 38. Alternatively, the phasing addition section 38 may correct the control signal supplied from the controller 30 according to the ambient sound velocity and perform the reception focusing process.

After carrying out correction of the attenuation due to the distance according to the depth of the reflection position of the ultrasonic waves on the reception data generated by the phasing addition section 38, the detection processor 40 generates B mode image data which is tomographic image information (brightness image information) in the subject by carrying out an envelope detection process.

The digital scan converter (DSC) 42 converts (raster converts) the B mode image data generated by the detection processor 40 into image data corresponding to a normal television signal scanning system.

The image processor 44 carries out various necessary image processing such as gradation processing on the B mode image data input from the DSC 42 to create B mode image data for display. The image processor 44 outputs the image processed B mode image data to the display controller 26 for display and/or stores the image processed B mode image data in the image memory 46.

The image memory 46 is a known storage (a storage medium) which stores the B mode image data processed by the image processor 44. The B mode image data stored in the image memory 46 is read out to the display controller 26 for display on the monitor 28 as necessary.

The display controller 26 uses the B mode image data on which the predetermined image process is carried out by the image processor 44 to display an ultrasound image on the monitor 28.

The monitor 28, for example, includes a display apparatus such as an LCD and displays an ultrasound image under the control of the display controller 26.

The controller 30 controls each section of the ultrasound diagnostic apparatus 10 on the basis of instructions input from the operating section 32 by an operator.

In addition, the controller 30 supplies various types of information input by an operator using the operating section 32 to necessary units. For example, in a case where information necessary for calculating the delay time used in the element data processor 22 and the phasing addition section 38 of the image generator 24 and information necessary for element data processing in the element data processor 22 are input by the operating section 32, the information is supplied to each section such as the transmission section 14, the reception section 16, the element data storage 20, the element data processor 22, the image generator 24, and the display controller 26 as necessary.

The operating section 32 is for the operator to perform an input operation and can be formed of a keyboard, a mouse, a trackball, a touch panel, or the like.
In addition, the operating section 32 is provided with an input function for the operator to input various types of information as necessary. For example, the operating section 32 is provided with an input function for inputting information of the probe 12 (the ultrasound transducer); information relating to the generation of the processed element data such as the transmission opening and the reception opening in the probe 12 (the transducer array 36), the number of element data to be superimposed, or the generation method; the focus point position of the ultrasonic beam; and the like.

The above are input, for example, by selecting the photograph site (the examination site), selecting the image quality, selecting the depth of the ultrasound image to be photographed, or the like.

The storage 34 stores information necessary for the controller 30 to operate and control the ultrasound diagnostic apparatus such as information relating to an operation program for the controller 30 to execute control of each section of the ultrasound diagnostic apparatus 10, the transmission delay pattern and the reception delay pattern, and the generation of processed element data; information on the probe 12 input from the operating section 32; information on the transmission opening, the reception opening, and the focus point position.

In the storage 34, it is possible to use a known recording medium such as a hard disk, a flexible disk, an MO, an MT, an RAM, a CD-ROM, or a DVD-ROM.

Here, in the ultrasound diagnostic apparatus 10, the element data processor 22, the sound velocity determiner 23, the phasing addition section 38, the detection processor 40, the DSC 42, the image processor 44, the display controller 26, and the like are configured by a CPU and an operation program causing the CPU to execute various processing. However, in the present invention, these units may be configured by a digital circuit.

As described above, the element data processor 22 generates processed element data by superimposing element data out of the element data (the unprocessed element data) stored in the element data storage 20 and obtained by a predetermined number (a plurality) of ultrasonic beam transmissions, for which the center ultrasound transducers (the center elements) are different and at least a portion of the transmission regions of the ultrasonic beams overlaps, according to the time of being received by each ultrasound transducer and the position of the ultrasound transducers.

Here, in the following description, the ultrasound transducers are also referred to simply as "elements".

Figure 3:
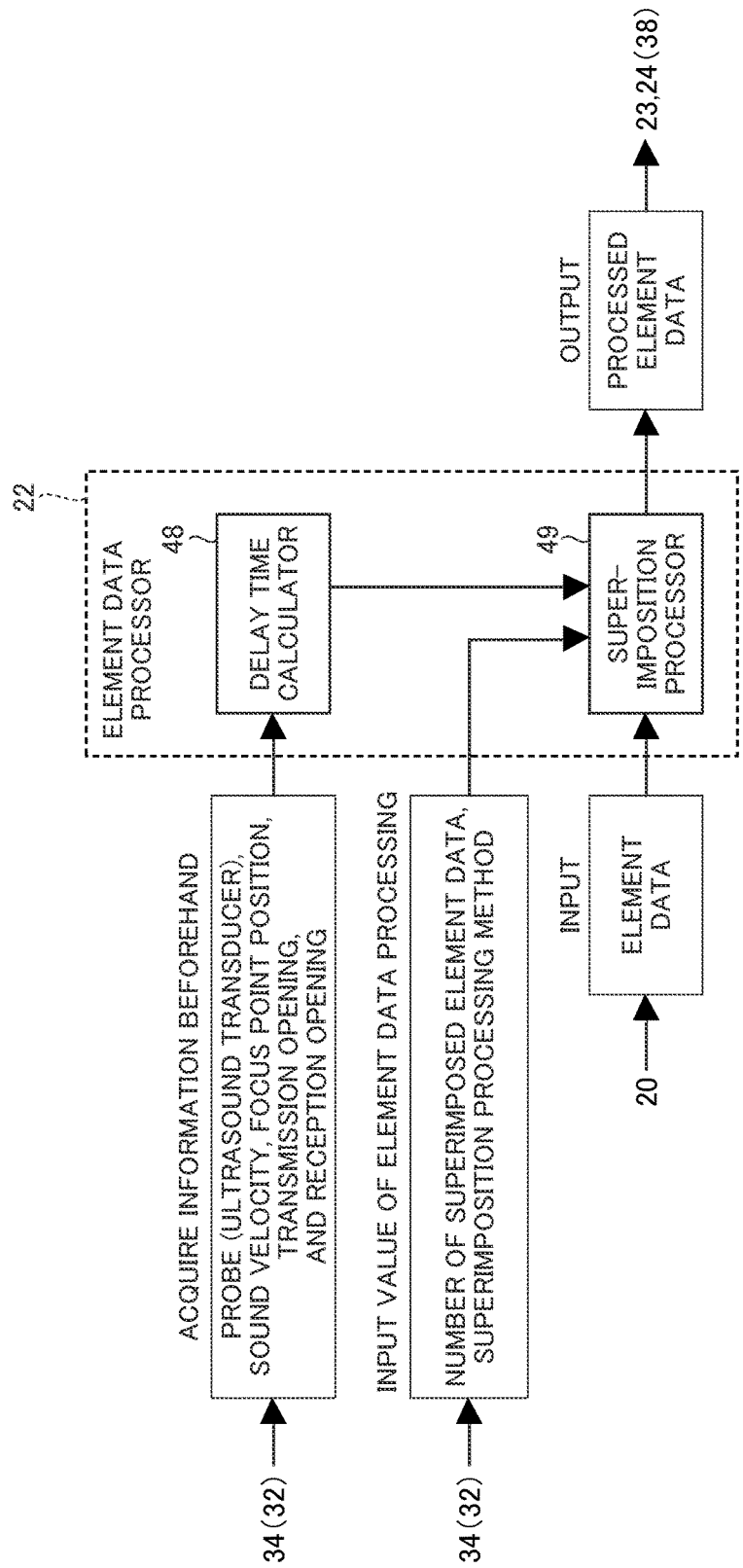
FIG. 3 is a block diagram conceptually illustrating an example of a configuration of an element data processor of the ultrasound diagnostic apparatus depicted in FIG. 1.

FIG. 3 is a block diagram conceptually illustrating the configuration of the element data processor 22.

As illustrated in FIG. 3, the element data processor 22 has a delay time calculator 48 and a superimposition processor 49.

The delay time calculator 48 acquires beforehand necessary information input from the operating section 32 or stored in the storage 34 after being input from the operating section 32. As this information, examples include information relating to the probe 12 (the ultrasound transducer (element)), focus point positions of the ultrasonic beams, the transmission opening and the reception opening of the probe 12, and the like.

In addition, the delay time calculator 48 calculates the delay time of the ultrasonic echoes received by the elements of the reception openings, that is, the element data, based on the geometric positions of the elements of the transmission openings which oscillate the ultrasonic waves in order to transmit (generate) the ultrasonic beams and the elements of the reception openings which receive the ultrasonic echoes from the subject.

The superimposition processor 49 reads out element data to be superimposed from the element data stored in the element data storage 20 based on information relating to the element data processing input from the operating section 32 or information relating to the element data processing stored in the storage 34 after being input from the operating section 32. Examples of the information relating to the element data processing include information relating to the number of element data to be superimposed, the superimposition processing method of the element data, and the like.

Here, in the present invention, the element data to be superimposed is element data obtained by ultrasonic beams where the transmission regions overlap and for which the center elements are different. In other words, the element data to be superimposed is two or more of element data generated for each of two or more target regions.

Furthermore, based on the delay time corresponding to each of the element data calculated by the delay time calculator 48, the superimposition processor 49 superimposes two or more of element data according to the reception time, that is, by matching the time and by matching the received absolute positions of the elements of the probe, thereby generating the processed element data.

Below, detailed description will be given of the processing of the element data performed by the element data processor 22.

Firstly, description will be given of a relationship between ultrasonic beams from the transmission elements and element data obtained by the reception elements in a case where, in the ultrasound probe 12, the ultrasonic beams are transmitted to the subject from the transmission opening, that is, the element (hereinafter, simply referred to as the transmission element) which sends out the ultrasonic waves in order to transmit the ultrasonic beams, and the element data is obtained by receiving the ultrasonic echoes generated by interaction with the subject in the reception opening, that is, in the element (hereinafter, simply referred to as the reception element) which receives the ultrasonic echoes.

As an example, as shown in FIG. 4A, the ultrasonic beams are transmitted with three elements 52c to 52e as transmission elements and the ultrasonic echoes are received with seven elements 52a to 52g as reception elements. Next, as shown in FIG. 4C, the ultrasonic beams are transmitted with three elements 52d to 52f as transmission elements by moving the elements by one element in the azimuth direction and each of the element data is acquired by receiving the ultrasonic echoes with seven elements 52b to 52h as the reception elements. Hereinafter, moving the elements in the azimuth direction, that is, moving the elements to be used in the azimuth direction, is also referred to as "shifting".

That is, the center element (the element in the center) is the element 52d in the example shown in FIG. 4A and the center element is the element 52e in the example shown in FIG. 4B.

Now, an ideal case will be considered in which ultrasonic beams 56 transmitted to the inspection object region including a reflection point 54 are converged at a focus point 58 and narrowed to the element intervals or less.

As shown in FIG. 4A, when ultrasonic beams 56 are transmitted from the elements 52c to 52e which are transmission elements with the element 52d directly above (on a straight line linking the reflection point and the focus point) the reflection point 54 as the center element and the element data is acquired by receiving the ultrasonic echoes in the elements 52a to 52g which are the reception elements, the focus point 58 of the ultrasonic beam 56 is on a straight line linking the element 52d which is the center element and the reflection point 54. In such a case, since the ultrasonic beam 56 is transmitted up to the reflection point 54, the ultrasonic echoes reflected from the reflection point 54 are generated.

The ultrasonic echoes from the reflection point 54 are received in the elements 52a to 52g which are the reception elements after passing through a receiving path 60 extending at a predetermined angle and the element data 62 as shown in FIG. 4B is obtained by the elements 52a to 52g. Here, in FIG. 4B, the vertical axis represents the time and the horizontal axis represents the position (the position of the elements) in the azimuth direction corresponding to FIG. 4A (the same applies to FIG. 4D).

In contrast, as shown in FIG. 4C, in a case where the center element is shifted by the amount of one element, the element 52e next to the element 52d directly above the reflection point 54 becomes the center element.

The ultrasonic beam 56 is transmitted from the elements 52d to 52f which are transmission elements with the element 52e as the center element and the ultrasonic echoes are received in the elements 52b to 52h which are the reception elements. At this time, in the same manner, when the ultrasonic beam 56 is ideal, the reflection point 54 is not present in the transmission direction of the ultrasonic beam 56, that is, on a straight line linking the center element 52e and the focus point 58. Accordingly, the ultrasonic beam 56 is not transmitted to the reflection point 54.

Therefore, the ultrasonic echoes reflected from the reflection point 54 are not generated and the elements 52b to 52h which are reception elements do not receive the ultrasonic echoes, thus, as shown in FIG. 4D, the element data is not obtained (the signal strength of the element data is "0").

However, since the actual ultrasonic beam is diffused after being converged at the focus point 58 as in an ultrasonic beam 64 shown in FIGS. 5A and 5C, the width is wider than the element interval.

Here, similar to FIG. 4A, in a case where the ultrasonic beam 64 is transmitted with the elements 52c to 52e as the transmission elements and the element 52d directly above the reflection point 54 as the center element as in FIG. 5A, even when the ultrasonic beam 64 is wide, the focus point 58 is on a straight line linking the element 52d and the reflection point 54. Accordingly, the ultrasonic beam 64 is reflected at the reflection point 54 and ultrasonic echoes are generated.

As a result, in the same manner as the case of FIG. 4A, the ultrasonic echoes from the reflection point 54 are received in the elements 52a to 52g which are the reception elements after passing through a receiving path 60 which widens at a predetermined angle, and, similarly, true element data 66 as shown in FIG. 5B is obtained.

Next, in the same manner as FIGS. 4A to 4D, as shown in FIG. 5C, the ultrasonic beam 56 is transmitted by shifting the center element by one element with the adjacent element 52e as the center element and the elements 52d to 52f as the transmission elements and the ultrasonic echoes are received with the elements 52b to 52h as the reception elements. Even in such a case, since the ultrasonic beam 64 is wide, even when the reflection point 54 is not present in the transmission direction of the ultrasonic waves, that is, on a straight line linking the element 52e which is the center element and the focus point 58, the ultrasonic beam 64 is transmitted to (arrives at) the reflection point 54.

Therefore, ultrasonic echoes which did not exist originally or so-called ghost reflected echoes are generated in the transmission direction of the ultrasonic beam from the reflection point 54. The ghost reflected echoes from the reflection point 54 are received in the elements 52b to 52h which are reception elements after passing through the receiving path 60 which widens at a predetermined angle as shown in FIG. 5C. As a result, ghost element data 68 as shown in FIG. 5D is obtained by the elements 52b to 52h.

In this manner, the ghost element data 68 is a cause of the precision of the ultrasound image generated from the element data decreasing.

The element data processor 22 calculates the delay time corresponding to the element data in the delay time calculator 48 and the superimposition processor 49 superimposes two or more of element data according to the delay time and the absolute position of the elements, whereby processed element data which is element data with high precision in which the ghost element data is attenuated by emphasizing the true element data is generated.

As described above, the delay time calculator 48 calculates the delay time of the element data received in each of the elements of the reception elements (reception openings).

That is, the propagation distance of the ultrasonic beam 64 shown in FIG. 5C is the sum of the transmission path where the ultrasonic beam 64 reaches the reflection point 54 from the element 52e which is the center element via the focus point 58 and the receiving path where the ghost reflected echoes from the reflection point 54 reach each of the elements 52b to 52h which are the reception elements.

The propagation distance of the ultrasonic beam 64 shown in FIG. 5C is longer than the propagation distance of the ultrasonic beam 64 shown in FIG. 5A, that is, the sum of the transmission path where the ultrasonic beam 64 reaches the reflection point 54 from the center element 52d via the focus point 58 and the receiving path where the true reflected echoes from the reflection point 54 reach the elements 52a to 52g which are the reception elements.

Therefore, the ghost element data 68 as shown in FIG. 5D is delayed with respect to the true element data 66 as shown in FIG. 5B.

In the delay time calculator 48 of the element data processor 22, the time difference between the true element data and the ghost element data, that is, the delay time is calculated from the sound velocity, the transmission elements, the focus point of the ultrasonic beam, the reflection point of the subject, and the geometric arrangement of the reception elements.

Accordingly, in the calculation of the delay time, information such as the shape of the probe 12 (the element interval, the probe being linear, convex, or the like), the sound velocity, the position of the focus point, the transmission opening, and the reception opening is necessary. In the delay time calculator 48, the information input by the operating section 32 or stored in the storage 34 is acquired to calculate the delay time. Here, the sound velocity may use a fixed value (for example, 1540 m/sec), may use a sound velocity (the ambient sound velocity) determined by the sound velocity determiner 23 to be described below, or may be input by the operator.

It is possible for the delay time to be calculated from the difference in the propagation time calculated according to the sound velocity and the total length (propagation distance) of the transmission path of the ultrasonic beam from the transmission element to the reflection point via the focus point and the receiving path of true reflected ultrasonic echoes or the ghost reflected signal from the reflection point up to the reception elements. Here, the transmission path of the ultrasonic beam is calculated from the geometric arrangement of the transmission elements, the focus point of the ultrasonic beam, the reflection point of the subject, and the reception elements.

Figure 6A:
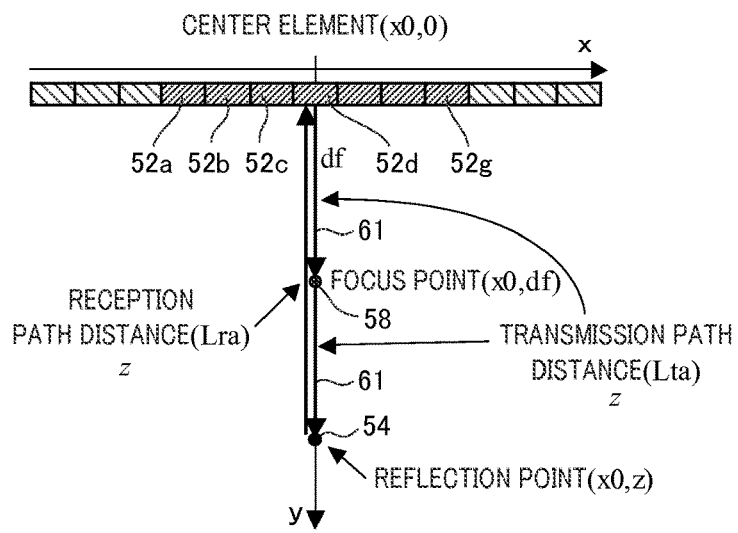
FIG. 6A and FIG. 6B are conceptual diagrams for describing a path of a sound wave in a case where the transmission and reception of ultrasonic waves is performed with respect to the same reflection point using center elements which are different from each other.
Figure 6B:
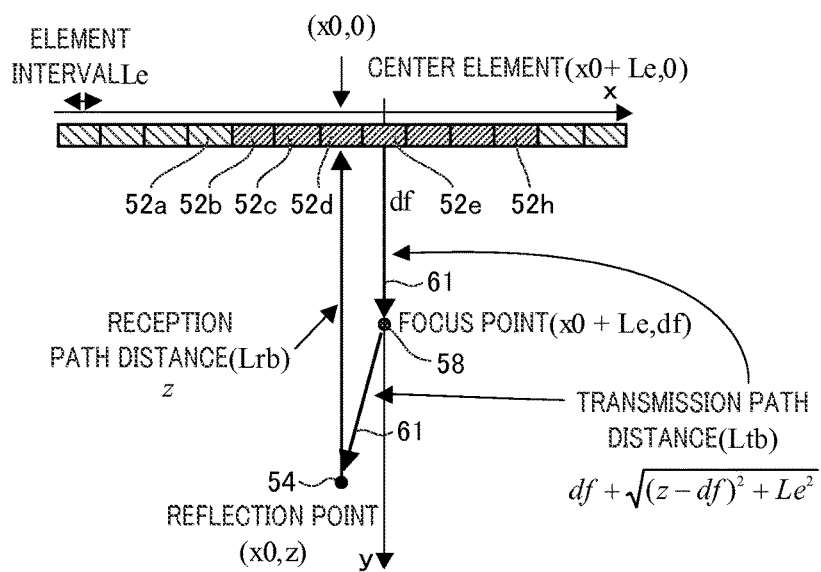

In the present invention, for example, as shown in FIG. 6A and FIG. 6B, it is possible to determine the length of the transmission path and the receiving path of the ultrasonic beam in the case of the true ultrasonic echoes and the ghost reflected echoes. Here, in FIG. 6, the x direction is the azimuth direction and the y direction is the depth direction.

In addition, in FIG. 6A, the transmission and reception of the ultrasonic waves is performed in the same manner as in FIG. 5A and, in FIG. 6B, the transmission and reception of the ultrasonic waves is performed in the same manner as in FIG. 5C.

In the case of the true ultrasonic echoes, as shown in FIG. 6A (FIG. 5A), the element 52d which is the center element, the focus point 58, and the reflection point 54 are positioned on a straight line. In other words, the positions of the element 52 which is the center element, the focus point 58, and the reflection point 54 are matched in the azimuth direction. That is, the focus point 58 and the reflection point 54 are positioned directly below the center element 52d. Accordingly, when the position of the element 52d which is the center element is taken to be coordinates (x0, 0) which are two dimensional x-y coordinates, the x coordinate of the focus point 58 and the reflection point 54 is also "x0". Below, the position of the focus point 58 in the transmission is taken to be coordinates (x0, df), the position of the reflection point 54 is taken to be coordinates (x0, z), and the interval of the elements is taken to be Le.

At this time, it is possible for the length (transmission path distance) Lta of a transmission path 61 of the ultrasonic beam from the element 52d which is the center element to the reflection point 54 via the focus point 58 and the length (the reception path distance) Lra of the receiving path 60 of the true reflecting ultrasonic echoes from the reflection point 54 to the element 52d to be calculated using Lta=Lra=z.

Accordingly, in the case of the true ultrasonic echoes, the propagation distance Lua of the ultrasonic echoes is Lua=Lta+Lra=2z.

Next, as shown in FIG. 6B, by shifting (shifting in the direction to the right in the diagram) the transmitting element and the reception element by one element in the x direction (the azimuth direction), transmission and reception are performed with the element 52e as the center element. As shown in FIG. 5C, in this case, the echoes reflected at the reflection point 54 are the ghost reflected echoes.

The reflection point 54 is positioned directly below (at the same position in the azimuth direction) the element 52d. Accordingly, as shown in FIG. 6B, in the transmission and the reception, the positions of Lhe element 52e which is the center element and the reflection point 54 in the x direction are shifted in the x direction by one element, that is, by Le.

Since the coordinates of the element 52d whose position matches the reflection point 54 in the x direction are (x0, 0), the coordinates of the element 52e which is the center element become (x0+Le, 0) and the coordinates of the focus point 58 in the transmission become (x0+Le, df). Here, as described above, the coordinates of the reflection point 54 are (x0, z).

Accordingly, it is possible for the length (the transmission path distance) Ltb of the transmission path 61 of the ultrasonic beam from the element 52e which is the center element to the reflection point 54 via the focus point 58 to be calculated by Ltb=df+$\sqrt{\{(z-df)^2+Le^2\}}$. On the other hand, it is possible for the length (the reception path distance) Lrb of the receiving path 60 of the ghost reflected signal from the reflection point 54 to the element 52d directly below (at the same position in the x direction=azimuth direction) to be calculated using the Lrb=z.

Accordingly, the propagation distance Lub of the ultrasonic waves in the case of the ghost reflected echoes is Lub=Ltb+Lrb=df+$\sqrt{\{(z-df)^2+Le^2\}}$+z.

In this manner, a value where the propagation distance Lua of the ultrasonic waves which is the total of the distance Lta of the transmission path 61 and the distance Lra of the receiving path 60 determined by the geometric arrangement shown in FIG. 6A is divided by the sound velocity is the propagation time of the true ultrasonic echoes. In addition, a value where the propagation distance Lub of the ultrasonic waves which is the total of the distance Ltb of the transmission path 61 and the distance Lrb of the receiving path 60 determined by the geometric arrangement shown in FIG. 6B is divided by the sound velocity is the propagation time of the ghost reflected echoes.

The delay time is determined from the difference between the propagation time of the true ultrasonic echoes when the x coordinates of the reflection point 54 and the center element are matched and the propagation time of the ghost reflected echoes when the x coordinates of the reflection point 54 and the center element are shifted by a single element interval at a time.

Here, the geometric model of FIG. 6A and FIG. 6B is a model where the transmission path 61 goes via the focus point 58; however, the present invention is not limited thereto, and, for example, may be a path arriving directly at the reflection point 54 without going via the focus point 58.

In addition, the geometric model of FIG. 6A and FIG. 6B is for the case of a linear probe; however, without being limited thereto, it is possible to perform the geometric calculation in the same manner from the shape of the probe even with other probes.

For example, in the case of a convex probe, it is possible to carry out the calculation in the same manner by setting the geometric model using the radius of the probe and angle of the element interval.

In addition, in the case of a steering transmission, it is possible to calculate the delay time of the true element data and the ghost element data of the surroundings thereof from the positional relationship between the transmission elements and the reflection points using a geometric model taking information such as the transmission angle into consideration.

Furthermore, without being limited to a method of calculating the delay time according to a geometric model, by determining the delay time for every measuring condition from the measuring results of measuring the high brightness reflection point in accordance with the measuring conditions of the apparatus in advance and storing the delay times in the apparatus, the delay time for the same measuring conditions may be read out.

Figure 6C:
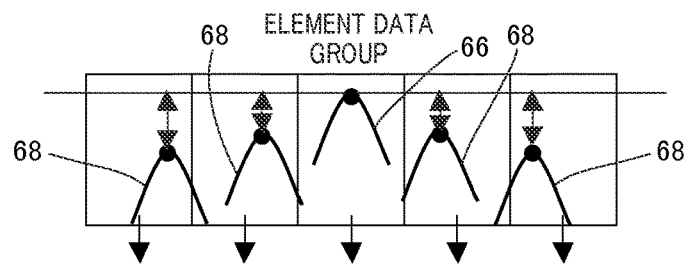
FIG. 6C is a conceptual diagram for describing element data obtained by a plurality of elements.

FIG. 6C shows the true element data 66 and the ghost element data 68.

In FIG. 6C, the center in the azimuth direction is the true element data 66, that is, element data obtained by transmission and reception where the positions of the center element and the reflection point 54 match in the x direction. In the example in the diagram, element data where the element 52$d$ is taken to be the center element is the true element data.

In addition, both sides of the center are ghost element data, that is, element data obtained by transmission and reception where the positions of the center element and the reflection point 54 do not match in the x direction. In the example in the diagram, element data where the element data 52$c$ or the element 52$e$ is taken to be the center element is the ghost element data.

Figure 6D:
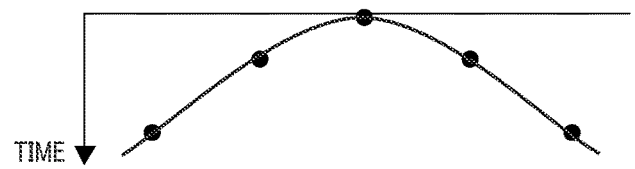
FIG. 6D is a conceptual diagram for describing each of the delay times of the element data depicted in FIG. 6C.

In addition, FIG. 6D shows an example of the delay time of the ghost element data 68 with respect to the true element data 66 obtained by the geometric calculation described above. Centering on the true element data 66, the element data 68 of the ghost signal indicates that the time is symmetrically delayed in the x direction, that is, the azimuth direction.

Here, in this manner, it is also possible for the delay time calculated in the delay time calculator 48 of the element data processor 22 to be used in the delay correction in the phasing addition section 38.

As will be described in detail below, in the present invention, by superimposing element data, which is obtained by the transmission of the ultrasonic beam where at least a portion of the ultrasonic beam overlaps and for which the center element is different, on element data, which is obtained by the transmission (the transmission and reception of the element of interest) of an ultrasonic beam where a certain element of interest is the center element, by matching the reception time of the ultrasonic echoes and the position of the elements, the processed element data (second element data) of the element of interest is generated. That is, the element data of the element of interest is rebuilt.

In FIG. 6, the reflection point 54 indicates the position (the output position of the element data) of a certain sampling point positioned directly below the element of interest, i.e., at the same position in the azimuth direction or on a straight line linking the element of interest and the focus point. In the present invention, the transmission and reception path to the sampling point in the transmission and reception of the element of interest is regarded as the transmission and reception path of the true element data and the transmission and reception path to the same sampling point in the transmission and reception (the transmission and reception from the surrounding elements) of the ultrasonic waves where the center element is different is regarded as the ghost transmission and reception path. The superimposition is performed by calculating the delay time from the difference between both transmission paths and matching the time of the element data using the delay time. In other words, the delay time is calculated and the superimposition of the element data is performed assuming that element data obtained by the transmission and reception of the element of interest is the true element data and element data obtained by the transmission and reception where the center element is different is the ghost element data.

In the present invention, the superimposition of the element data is performed by calculating the delay time with the same concept corresponding to all of the sampling points (the output position of all the element data) and the processed element data of each of the elements is generated.

Here, in fact, even when the positions of the sampling points (reflection points) are shifted in the azimuth direction (the x direction), the length of the receiving path (the reception path distance Lrb) does not change. Accordingly, in relation to each of the elements of interest, the calculation of the delay times of the element data according to transmission and reception for which the center elements are different may be performed for every sampling point in the depth direction (the y direction).

In addition, it is not necessary to know which element data the true element data is in the superimposition process. That is, although described in detail with reference to FIGS. 7A to 7H below, in the superimposition processing, the element data of the element of interest is automatically emphasized and remains when the element data is the true element data and the element data is cancelled when the element data is ghost element data. That is, in a case where the element data of the element of interest is the true element data, the signal is emphasized by matching the processing according to the delay time and, in a case where the element data of the element of interest is the ghost element data, the signal is cancelled without matching the processing according to the delay time.

Next, in the superimposition processor 49 of the element data processor 22 of the present invention, the superimposition processing of the element data is performed using the delay time calculated in the delay time calculator 48 in this manner.

Here, in the superimposition processing in the superimposition processor 49, information on the superimposition processing method and the number of superimposition element data at the time of the superimposition is necessary; however, this information may be input using the operating section 32 in advance, or may be stored in the storage 34 in advance.

FIGS. 7A to 7H show an example of the superimposition processing performed in the superimposition processor 49. Here, the examples shown in FIGS. 7A to 7H are of a case where the number of element data is five and the number of superimposition element data is three.

FIG. 7A shows five element data obtained by carrying out five sets of transmission and reception of the ultrasonic waves lined up side by side. In addition, FIG. 7A represents a state where ultrasonic echoes are received after the ultrasonic beams are transmitted for each element data. The horizontal axis of each element data represents a reception element and displays the center element in the center in the transmission and reception of the ultrasonic beam in each of the element data. The vertical axis represents the reception time. In this example, five sets of transmission and reception of the ultrasonic waves are performed by shifting the center element by one element at a time, for example, in the previous elements 52b to 52f or the like.

FIG. 7A shows a state where one reflection point is present only directly below the center element in the center element data. That is, out of the five element data, the true ultrasonic echoes are received in the element data in the middle from the reflection point in the transmission and reception of the ultrasonic waves. That is, the element data in the middle is the true element data.

Regarding the two element data on both sides other than the element data in the middle, the reflection point is not present directly below the center element in the transmission and reception of the ultrasonic waves. However, due to the ultrasonic beam hitting the reflection point which is present directly below the transmission element of the element data in the middle according to the spread of the transmitted ultrasonic beam, the generated reflected echo element data, that is, the ghost element data bleeds through.

The further the ghost element data is separated from the true element data, the longer the propagation time of the ultrasonic waves up to the reflection point, thus the reception time for the ghost element data is longer than for the true element data. In addition, the position of the reception element where the ultrasonic echoes from the reflection point are first received is directly above the reflection point (an element whose position in the azimuth direction matches the reflection point).

Here, the horizontal axes of each of the element data in FIGS. 7A to 7H set the center element during the transmission of the ultrasonic beam in the center. Accordingly, in the examples shown in FIGS. 7A to 7H, since transmission is carried out by shifting the center element by one element for each of the element data, the absolute position of the elements in the azimuth direction in each element data is shifted by one element at a time. In other words, in the element data in the middle, the reception element which first receives the reflected signal from the reflection point is the center element; however, in both adjacent element data, the reception element is shifted by one element from the element data in the middle, the element data on the right side is shifted by one element to the left, and the element data on the left side is shifted one element to the right. Furthermore, the element data on both ends is shifted by two elements from the element data in the middle, the element data at the right end is shifted by two elements to the left, and the element data at the left end is shifted by two elements to the right. In this manner, not only is the reception time longer for the ghost signal than for the true signal, but shifting is also generated with respect to the direction of the reception elements.

FIG. 7B shows an example of the delay time of the reception time with respect to the element data in the middle of the element data of the five elements shown in FIG. 7A.

In the superimposition processor 49, in a case where the center element of the element data in the middle is set as the element of interest using the delay time shown in FIG. 7B, delay time correction is performed according to the number of elements to be superimposed (three elements in the example in the diagram) centering on the element of interest. Also, by shifting by several elements (one element at both sides in the example in the diagram) from the element of interest in the azimuth direction, that is, by matching the phases, element data for three elements are superimposed and determined as one superimposition processed element data for the element of interest.

That is, in the present example, the processed element data of the element data of the element of interest is generated by superimposing the element data obtained by transmission and reception of the ultrasonic waves where the element adjacent to the element of interest is the center element on the element data obtained by the transmission and reception of the ultrasonic waves where the element of interest is the center element.

Hereinafter, the element data obtained by transmission and reception of the ultrasonic waves where the element of interest is the center element is also referred to as "element data of the element of interest," and the element data obtained by transmission and reception of the ultrasonic waves where the element adjacent to the element of interest is the center element is also referred to as the "element data of the adjacent element."

The superimposition processed element data of the element of interest obtained in this manner is shown in FIG. 7C.

As described above, the element data of the element interest shown in FIG. 7A is true element data in which the reflection point is present directly below the center element (that is, the element of interest). In addition, the element data obtained by the transmission and reception of ultrasonic waves where an element adjacent to the element of interest is the center element is also ultrasonic echo data where the ultrasonic waves are incident on the reflection point and reflected.

Accordingly, when performing the phase matching by carrying out delay time correction and azimuth direction shifting on the element data of the elements adjacent at both sides of the element of interest, the element data of the adjacent element and the element data of the element of interest overlap at a high brightness position since the phases match as shown in FIG. 7C. Therefore, for example, when the element data are added, the element data value indicates a large value (high brightness value). For instance, the element data indicates an emphasized value (high brightness value) even when an average value is determined by averaging.

In contrast, FIG. 7D shows an example of a case with the same element data as FIG. 7A; however, the center element of the element data adjacent to the left of the element data in the middle is the element of interest. That is, this example shows a case of the transmission and reception of ultrasonic waves where an element for which the reflection point is not present directly below is the center element, in which the center element is the element of interest. Accordingly, the element data where the element is the center element is ghost element data.

FIG. 7E is the same as FIG. 7B and shows an example of the delay time of the reception time with respect to the element data in the middle of the element data of five elements shown in FIG. 7A. That is, since FIG. 7A and FIG. 7D are of the same element data, the delay time of the reception time with respect to the element data in the middle of the element data of five elements shown in FIG. 7D is also the same.

In the superimposition processor 49, the delay time correction is performed for the number of superimposed elements centering on the element of interest using the calculated delay time. Also, by shifting by a number of elements from the element of interest in the azimuth direction, the unprocessed element data for the number of superimposition elements are superimposed and determined as one superimposition processed element data for the element of interest. In the example in the diagram, the delay time correction is performed for three elements centering on the element of interest using the delay time shown in FIG. 7E (that is, the same as FIG. 7B). Also, by shifting by one element in the azimuth direction at both sides, unprocessed element data for the three elements are superimposed and determined as one superimposed element data for the element of interest.

The superimposed element data of the element of interest obtained in this manner is shown in FIG. 7F.

The element data of the element of interest shown in FIG. 7D is ghost element data. Therefore, even when phase matching is performed by performing delay time correction and azimuth direction shifting on the unprocessed element data of the adjacent elements on both sides of the element of interest, as shown in FIG. 7F, each element data of the adjacent elements and the element data of the element of interest do not overlap because the phases do not mutually match. For this reason, since the phases do not match even when, for example, three element data are added, signals or the like where the phases are inverted cancel each other out. As a result, the added value is not large and, for example, a small value is indicated when the average value is determined by averaging.

With regard to the five elements in the example in the diagram, FIG. 7G shows an overlapping state of element data of three adjacent elements when the same delay time correction and azimuth direction shifting corresponding to the element of interest are performed for the other element data. In addition, FIG. 7H shows the results after, for example, an addition processing or an averaging processing is carried out as the superimposition processing on the element data of the 3 elements.

As shown in FIG. 7H, in a case where a center element where the reflection point is present directly below shown in FIG. 7A is the element of interest, the element data of the true signal is determined as superimposed element data having a high brightness value. In contrast, in all four elements of each of the two elements on both sides thereof, for the ghost element data, the element data where the phases do not match each other are added or averaged. Therefore, the element data cancel each other out and, due to this, the value of the ghost superimposed element data is lower than that of the superimposed element data having a high brightness value which is element data of a true signal. As a result, it is possible to reduce the influence of the ghost element data on the true element data, or it is possible to reduce the influence thereof to a level which may be ignored.

That is, one or more of the element data which is obtained by transmission and reception of the ultrasonic waves for which the transmission regions of the ultrasonic beam overlap and for which the center elements are different are superimposed on element data (element data of the element of interest) where a certain element is set as the element of interest and which is obtained by transmission of an ultrasonic beam where this element of interest is the center element by carrying out time and position matching, and processed element data corresponding to the element data of the element of interest is generated. Due to this, the brightness level of the true element data is increased and it is possible to decrease the ghost element data. In other words, by performing rebuilding (correction) of the element data of the element of interest using element data according to transmission and reception where at least a portion of the ultrasonic beam overlaps and the center element is different, the brightness level of the true element data is increased and it is possible to decrease the ghost element data.

Therefore, as will be described below, according to the present invention which performs determination of the sound velocity using the element data in the vicinities of the focus point and using processed element data in the other regions, it is possible to determine the sound velocity in the subject with high precision by eliminating the influence of the ghost and using element data in such a case that the focus points are linked at a large number of points on the sound ray to be transmitted, that is, element data (the reception data (ultrasound image data)) obtained by the transmission of the ultrasonic waves at multiple virtual focus points.

In addition, similarly, since it is possible to generate the ultrasound image with element data where the influence of the ghost is eliminated by performing phasing addition or a detection process on the processed element data, generating the reception data, and generating the ultrasound image, it is possible to generate an ultrasound image with high image quality, high brightness, and excellent sharpness. In other words, since it is possible to generate the ultrasound image with element data in such a case that the focus points at all points on the sound ray are linked by performing phasing addition or a detection processing on the processed element data, generating the reception data, and generating the ultrasound image, it is possible to generate an ultrasound image with high image quality, high brightness, and excellent sharpness.

Here, the generation of the processed element data is also referred to as a multiline process in the following description.

In the present invention, the center element is the element in the center in the azimuth direction in a case where the number of openings of the transmission (the number of elements which perform the transmission of the ultrasonic waves) is an odd number.

On the other hand, calculation may be performed by any one of the elements in the center in the azimuth direction being the center element in a case where the number of openings is an even number, or by having a focus point on a line in the middle of the openings in a case where an element in the middle of the azimuth direction is assumed to be the center element, that is, where the number of openings is an even number.

Here, as the superimposition processing method in the superimposition processor 49, an average value or a median value may be taken instead of only adding, or addition may be carried out after multiplication with a coefficient. Here, taking the average value or the median value may be considered equivalent to applying an averaging filter or a median filter at the element data level; however, an inverse filter or the like which performs a normal image process may also be applied instead of the averaging filter or the median filter.

Alternatively, when each of the element data to be superimposed is compared, the value is the maximum in a case where the element data are similar, the value is average in a case where the element data are not similar, and the value is intermediate in a case where the distribution is biased, but the superimposition processing may be changed based on the feature amount of each of the element data to be superimposed without being limited thereto.

In addition, the number of element data to be superimposed on the element data of the element of interest is not limited two in the example in the diagram and may be one or may be three or more. That is, the number of the element data to be superimposed on the element data of the element of interest may be appropriately set according to the required processing speed (the frame rate or the like), image quality, or the like.

Here, it is desirable that the number of element data to be superimposed on the element data of the element of interest match the extent of the spread of the beam width of the ultrasonic beam. Accordingly, in a case where the beam width changes according to the depth, the number of the element data to be superimposed may also be changed according to the depth.

In addition, since the beam width depends on the number of transmission openings, the number of element data to be superimposed may be changed according to the number of the transmission openings. Alternatively, the number of element data to be superimposed may be changed based on the feature amount such as the brightness value of the image and, in addition, the optimum number of element data to be superimposed may be selected from an image created by changing the number of element data to be superimposed into a plurality of patterns.

Here, in the multiline processing above, the processed element data of the element data of the element of interest is generated by superimposing the element data where the center elements are different and which is obtained by a transmission of a plurality of ultrasonic beams for which the transmission direction of the ultrasonic beams is parallel (the angles are the same); however, the present invention is not limited thereto.

For example, the processed element data may be generated by superimposing the element data where the center elements are the same and which is obtained by the transmission of a plurality of ultrasonic beams where the transmission directions (angles) are different. At this time, whether to generate the processed element data of the element data obtained by the transmission of any ultrasonic beam (that is, whether to generate the processed element data of the sound ray in any direction) may be set by default according to the examination site, the type of probe, or the like, or may be selected by the operator.

In addition, the processed element data may be generated using both of the element data where the center elements are different and which is obtained by the transmission of parallel ultrasonic beams and the element data where the center elements are the same and which is obtained by the transmission of ultrasonic beams with different transmission directions.

As described above, the element data processor 22 sends the generated processed element data to the image generator 24 (the phasing addition section 38). In addition, when determining (updating) the sound velocity of the subject, the element data processor 22 sends the generated processed element data to the sound velocity determiner 23 or the image generator 24.

In the image generator 24 to which the processed element data is supplied, as described above, the reception data is generated by performing a reception focusing process by the phasing addition section 38 carrying out phasing addition on the processed element data. Next, the detection processor 40 generates B mode image data by carrying out attenuation correction and an envelope detection processing on the reception data.

In addition, in the image generator 24, the DSC 42 raster converts the B mode image data into image data corresponding to a normal television signal scanning method and carries out a predetermined process such as a gradation processing in the image processor 44.

The image processor 44 stores the generated B mode image data in the image memory 46 and/or sends the generated B mode image data to the display controller 26 to display a B mode image of the subject on the monitor 28.

On the other hand, the sound velocity determiner 23 determines the sound velocity (calculates the sound velocity) the ultrasonic waves in the subject using the supplied processed element data.

Figure 8:
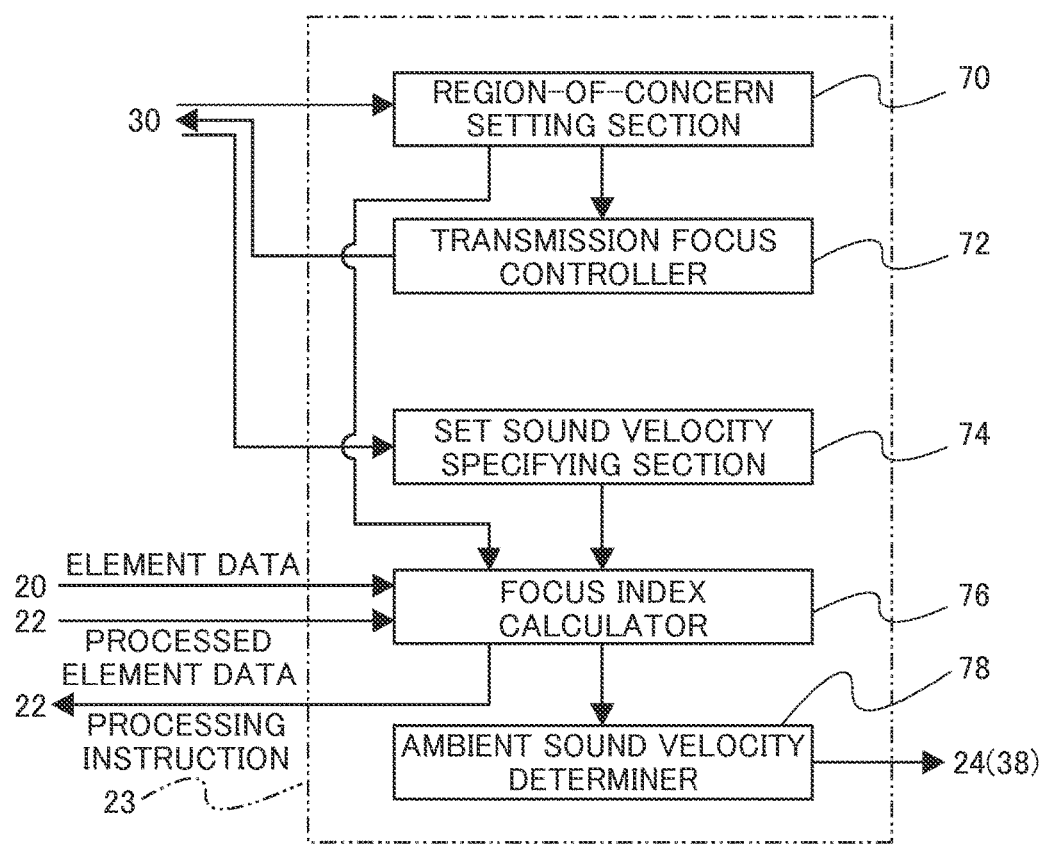
FIG. 8 is a block diagram conceptually illustrating an example of a configuration of a sound velocity determiner of the ultrasound diagnostic apparatus depicted in FIG. 1.

FIG. 8 is block diagram conceptually showing the configuration of the sound velocity determiner 23.

As shown in FIG. 8, the sound velocity determiner 23 has a region-of-concern setting section 70, a transmission focus controller 72, a set sound velocity specifying section 74, a focus index calculator 76, and an ambient sound velocity determiner 78.

The region-of-concern setting section 70 sets the region of concern in the B mode image (in the ultrasound image) according to instructions from the controller 30. In the sound velocity determiner 23, the sound velocity of the subject is determined for every region of concern.

In the present embodiment, the region-of-concern setting section 70 divides the entire screen of the B mode image (the inspection region in the subject) into a grid pattern and individually sets the regions of concern.

The number of divisions (the number in the grid) may be set in advance by default or it may be possible for the operator to optionally set the number in the azimuth direction and/or the depth direction. In a case where the number of divisions is set by default, there may be different settings for each image size or observation site. Furthermore, it may be possible for the operator to select from a plurality of divisions set in advance.

Here, in the present invention, the region of concern is not limited to each region of the grid into which the B mode image is divided.

For example, all of the pixels (the positions (regions) corresponding to all of the pixels) generating the reception data (B mode image data) may be set as regions of concern. In other words, in an aspect where the screen is divided as described above, the screen may be divided into a grid corresponding to all of the pixels generating the reception data.

Alternatively, instead of the entire screen, a part of the screen which is set in advance or selected from a plurality of choices may be divided into a grid and parts thereof individually set as regions of concern. In addition, instead the entire screen, the region of concern may be set in correspondence with an ROI set by the operator. Here, even in a case where the region of concern is set in a part of the screen or in the ROI, the division may be performed in the same manner as for the entire screen described above. In addition, it may be possible for the setting of the region of concern in the entire screen and the setting of the region of concern in the ROI to be selected by the operator.

In addition, the form of the division is not limited to a grid, for example, in the case of a B mode image with a fan shape such as an ultrasound image according to a convex probe, the form of the division may also be set to a fan shape according to this. In such a case, it is also possible to use each aspect described above.

Here, the region of concern may be changed or updated in a case where the image is greatly changed, a case where the observation conditions are changed such as changes in the observation magnification or changes in the observation depth, or the like. Example of the case where the image is greatly changed includes a case where the change value of the image feature amount exceeds a threshold, or the like.

Furthermore, the changes or the updates to the region of concern may be instructed by the operator.

The region-of-concern setting section 70 also sets a focus point (the position of the focus point) in order to transmit (transmission focus) the ultrasonic waves corresponding to the determination of the ambient sound velocity with respect to a set region of concern.

The focus point may be set by default in advance according to the observation site, the number of sound rays, the number of transmission and reception openings, the type of the probe 12, or the like. Alternatively, the operator may select or input instructions for the focus points. Furthermore, it may be possible to select between the setting of the focus points by default and the instruction of the focus points by the operator.

Here, as described above, with the present invention which performs determination of the sound velocity using the processed element data where the superimposition of the element data is performed, it is possible to perform the transmission using multiple virtual focus points. Therefore, a plurality of positions of the focus points may be set with respect to one sound ray; however, one focus point is basically sufficient for one sound ray. Thus, according to the present invention, it is possible to perform the determination of the sound velocity without reducing the frame rate. Here, one sound ray refers to the transmission and reception of the ultrasonic waves in the same direction corresponding to one center element, that is, to one scanning line.

In addition, the position of the focus points may be the same for all of the sound rays or sound rays with different focus points may be mixed in.

When setting the region of concern and the focus point in this manner, the region-of-concern setting section 70 sends the information on the set region of concern and the focus point (the position of the focus point) to the transmission focus controller 72 and the focus index calculator 76.

The transmission focus controller 72 sends a transmission focus instruction to the controller 30 for the transmission section 14 to perform the transmission focus according to the region of concern and the focus point set by the region-of-concern setting section 70.

The set sound velocity specifying section 74 specifies a set sound velocity in order to perform reception focusing with respect to the reception data in the determination of the ambient sound velocity under the control of the controller 30.

The focus index calculator 76 calculates the focus index of the reception data by performing reception focusing with respect to the reception data for each of a plurality of set sound velocities specified by the set sound velocity specifying section 74 using the element data stored n the element data storage 20 or the processed element data generated by the element data processor 22.

Specifically, the focus index calculator 76 determines whether or not the region of concern is in the vicinity of a focus point using the information on the region of concern and the focus point supplied from the region-of-concern setting section 70. As a result, in a case where the region of concern is in the vicinity of the focus point, the focus index is calculated using the element data, and, for other regions of concern, instructions are given to perform a multiline processing to the element data processor 22 and the focus index is calculated using the processed element data.

Here, in the present invention, the vicinity of the focus point is a position (including the focus point) within 10 mm from the position of the focus point.

The ambient sound velocity determiner 78 determines the ambient sound velocity of the region of concern based on the focus index for each of a plurality of set sound velocities.

Figure 9:
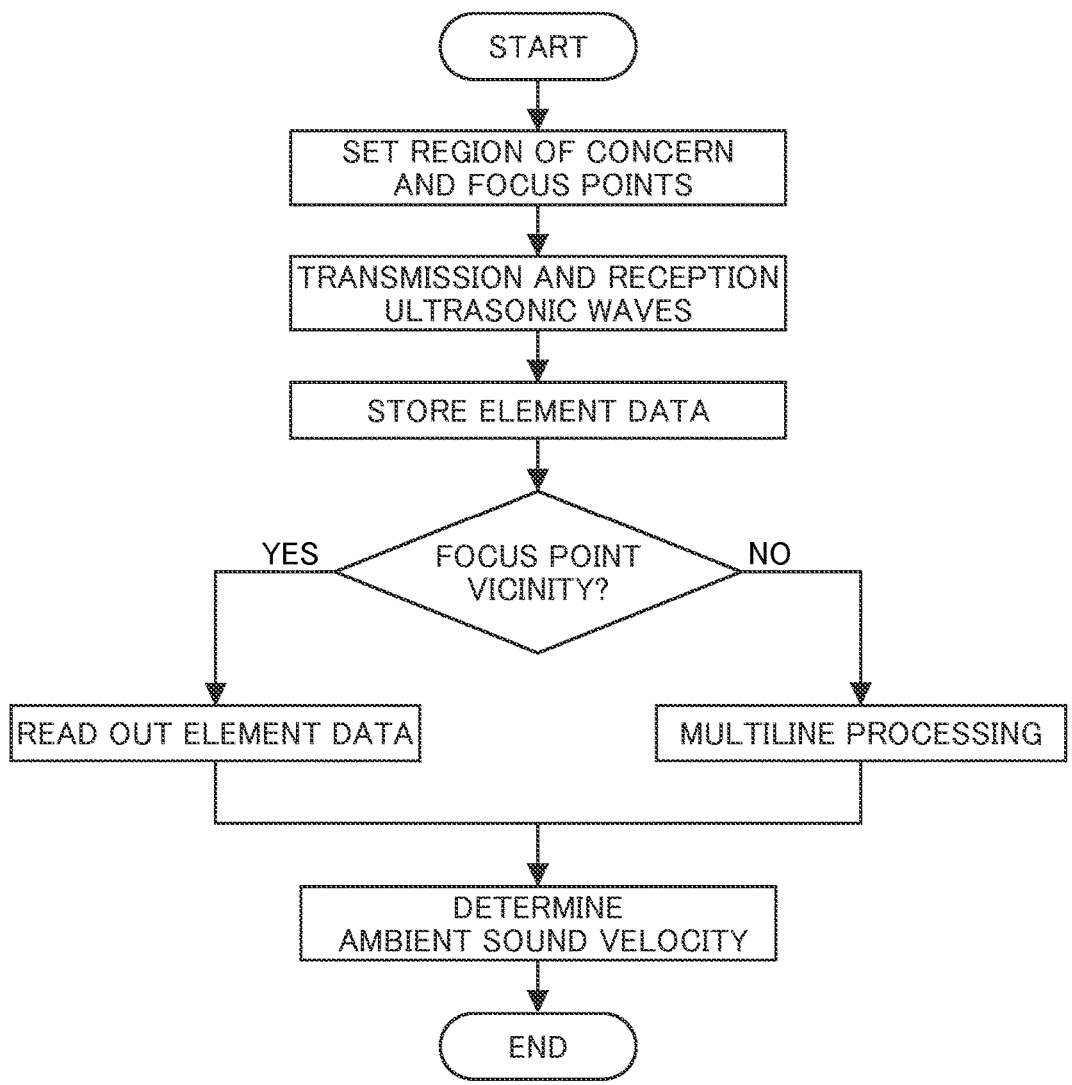
FIG. 9 is a flow chart for describing an example of a sound velocity determining process of the ultrasound diagnostic apparatus depicted in FIG. 1.

Below, with reference to the flow chart shown in FIG. 9, detailed description will be given of the method of determining the sound velocity in the ultrasound diagnostic apparatus 10 (the sound velocity determining method of the present invention).

The recording medium of the present invention is a computer-readable recording medium which makes a computer execute the following sound velocity determining method in the ultrasound diagnostic apparatus 10.

In the ultrasound diagnostic apparatus 10, when determining the ambient sound velocity, first, the region-of-concern setting section 70 sets the region of concern and the focus point according to instructions from the controller 30 as described above.

The region-of-concern setting section 70 supplies the set region of concern and the focus point information to the transmission focus controller 72 and the focus index calculator 76.

Here, in the present invention, the timing at which the ambient sound velocity is determined (the update timing of the ambient sound velocity) is not particularly limited and may be the same as for a known ultrasound diagnostic apparatus. For example, the determination of the ambient sound velocity may be performed only one time according to the measurement start instructions. Alternatively, the determination of the ambient sound velocity may be performed in a case where the image is greatly changed (in a case where a change value of a feature amount of the image exceeds a threshold, or the like). Alternatively, the determination of the ambient sound velocity may be performed every predetermined number of frames determined as appropriate or every time a predetermined time passes. Alternatively, the determination of the ambient sound velocity may be performed according to the input instructions of the operator. Alternatively, it may be possible to appropriately select two or more timings for the sound velocity determination.

Regardless of the timing at which the ambient sound velocity is determined, in the present invention, the ambient sound velocity is determined using the element data for the focus point vicinity and the ambient sound velocity is determined using the processed element data obtained by a multiline processing for the other regions. According to the present invention, basically, since the transmission may be performed at one focus point with respect to one sound ray, in contrast to the related art, a decrease in the frame rate caused by the determination of the sound velocity is avoided. Here, as described above, the one sound ray is the transmission and reception of ultrasonic waves in the same direction corresponding to one center element, that is, one scanning line.

According to the setting of the region of concern, the transmission focus controller 72 sends a transmission focus instruction to the controller 30 so that the transmission section 14 executes the transmission focus to transmit the desired ultrasonic beam to the set region of concern and focus point.

Accordingly, the transmission section 14 transmits the ultrasonic beam to the subject by driving the ultrasound transducers (elements) corresponding to the transducer array 36 in the probe 12, the ultrasonic echoes reflected by the subject are received by the ultrasound transducers (elements), and an analog reception signal is output to the reception section 16.

The reception section 16 carries out a predetermined process such as amplification on the analog reception signal and supplies the result to the A/D converter 18.

The A/D converter 18 A/D converts the analog reception signal supplied from the reception section 16 and sets the signal as element data which is a digital reception signal. The element data is stored in the element data storage 20.

On the other hand, when the storage of the element data in the element data storage 20 is started, the focus index calculator 76 performs determination of whether or not each region of concern is in the vicinity of the focus point using the information of the region of concern and the focus point of the ultrasonic beam supplied from the region-of-concern setting section 70.

The focus index calculator 76 sends out instructions to the element data processor 22 so as to perform multiline processing on element data of the region of concern (No) other than the focus point vicinity according to the results of the determination. In addition, the focus index calculator 76 reads out the element data from the element data storage 20 in relation to the region of concern (Yes) in the vicinity of the focus point.

The element data processor 22 which receives the instructions for the element data on which the multiline processing is performed from the focus index calculator 76 reads out the corresponding element data from the element data storage 20 and generates the processed element data by performing the multiline processing described above.

That is, as shown in FIGS. 7A to 7H, with regard to the element of interest and both adjacent elements, the element data processor 22 calculates the delay time of the element data of both adjacent elements with respect to the element data of the element of interest, performs delay time correction and azimuth direction shifting on the element data of the adjacent element, and generates the processed element data of the element of interest by superimposing the element data of the adjacent elements on both sides on the element data of the element of interest.

The element data processor 22 supplies the generated processed element data to the sound velocity determiner 23 (the focus index calculator 76).

Here, in the present invention, the processed element data (the element data) generated for the sound velocity determination may be used only in the sound velocity determination.

However, in the ultrasound diagnostic apparatus 10, the element data processor 22 also supplies the processed element data generated for the sound velocity determination to the image generator 24, and the image generator 24 may generate an ultrasound image using the processed element data. In this process, the element data of the element data storage 20 is used for a portion where the processed element data is insufficient.

Accordingly, in a case where the ultrasound image is generated using the processed element data for the sound velocity determination, the multiline processing may be performed on the element data in the vicinity of the focus point and not only on the element data other than in the vicinity of the focus point. At this time, the element data processor 22 supplies only the processed element data of the element of interest other than in the vicinity of the focus point to the sound velocity determiner 23. Alternatively, the element data processor 22 supplies all the processed element data to the sound velocity determiner 23 and the sound velocity determiner 23 may select the processed element data to be used in the determination of the ambient sound velocity according to whether or not the data is in the vicinity of the focus point. Furthermore, at this time, the element data processor 22 may perform generation of the processed element data automatically at the point of time at which the element data storage 20 starts the storage of the element data even when there is no instruction from the focus index calculator 76.

The sound velocity determiner 23 determines the sound velocity of the ultrasonic waves in the subject using the supplied processed element data or the element data read out from the element data storage 20.

Figure 10:
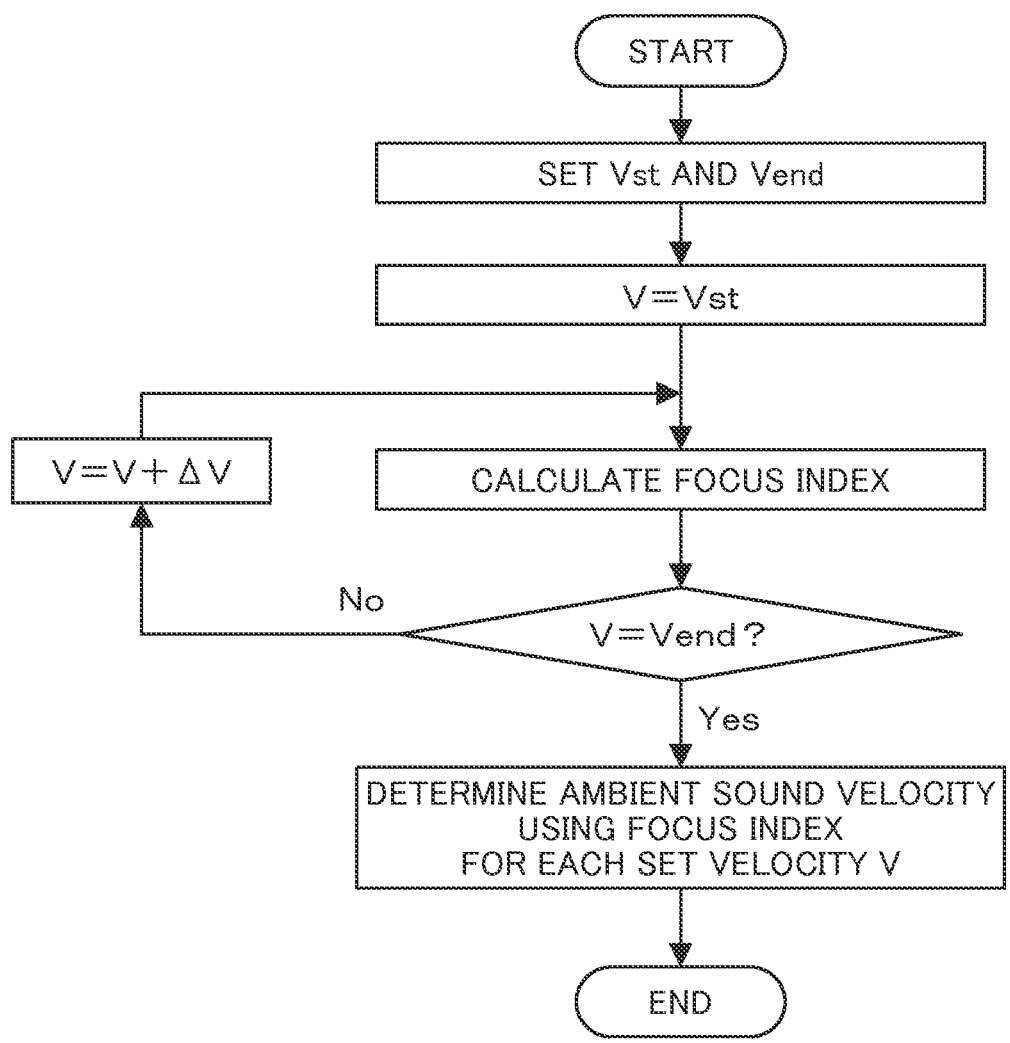
FIG. 10 is a flow chart for describing a sound velocity determining method in the flow chart of FIG. 9.

FIG. 10 shows a flow chart of an example of the sound velocity determining method in the sound velocity determiner 23. Here, in the present invention, the sound velocity determining method in the sound velocity determiner 23 is not limited to this method and it is possible to use various sound velocity determining methods (methods of calculating the sound velocity) performed in the ultrasound diagnostic apparatus.

When the element data or the processed element data is supplied, the element data or the processed element data are stored in a predetermined site in the sound velocity determiner 23 if necessary. Also, first, the set sound velocity specifying section 74 sets the starting sound velocity Vst and the finishing sound velocity Vend of the set sound velocity V and further sets the starting sound velocity Vst of the set sound velocity V. The set sound velocity including the starting sound velocity Vst and the finishing sound velocity Vend may be set by default in advance.

Alternatively, by the operator optionally inputting only the starting sound velocity Vst and the finishing sound velocity Vend, only the step width therebetween (a predetermined step sound velocity amount $\Delta V$) may be set by default. Alternatively, the operator may carry out the inputting optionally. In addition, in a case where the set sound velocity or the step width is set by default, a plurality of types of set sound velocities are set according to the observation site, the gender of the subject, or the like, and can be selected as appropriate by the operator.

In the present example, as an example, 1410 m/sec is set as the starting sound velocity Vst and 1570 m/sec is set as the finishing sound velocity Vend and, accordingly, the set sound velocity V is set at intervals of 40 m/sec as the predetermined step width.

Next, the focus index calculator 76 calculates the focus index of the reception data by performing the reception focusing processing on the element data or the processed element data for each of a plurality of set sound velocities specified by the set sound velocity specifying section 74 corresponding to each of the regions of concern.

Specifically, for the reception data (the ultrasound image data/ultrasound image) in the region of concern, the focus index calculator 76 calculates the integrated value, a squared integral value, a peak value, a degree of sharpness (sharpness), a contrast, a brightness value, a half-width, a frequency spectrum integration, a maximum value, a frequency spectrum integral value or squared integral value normalized by a DC component, an autocorrelation value, or the like as the focus index.

Next, the sound velocity determiner 23 determines whether or not the set sound velocity V reached the finishing sound velocity Vend in the set sound velocity specifying section 74. As a result, if the set sound velocity V is less than the finishing sound velocity Vend (No), the focus index of the region of concern is calculated by adding the predetermined step sound velocity amount $\Delta V$, that is, 40 m/sec in the present example to the set sound velocity V.

This routine is repeated and when it is determined that the set sound velocity V has reached the finishing sound velocity Vend (Yes), the ambient sound velocity of the region of concern is determined by the ambient sound velocity determiner 78 based on the focus index for each of the plurality of set sound velocities by setting the set sound velocity with the highest focus index as the ambient sound velocity of the region of concern, or the like. For example, by setting the brightness of the ultrasound image as the focus index, the set sound velocity V obtained by the ultrasound image with the highest brightness in the region of concern is set as the ambient sound velocity of the region of concern.

That is, the ambient sound velocity in the present example is the average sound velocity of a region between the ultrasound probe 12 and the region of concern when the sound velocity from the probe 12 (the transducer array 36 (ultrasound transducers)) to a certain region of concern is assumed to be constant. As described above, the sound velocity determiner 23 performs the determination of the ambient sound velocity in this manner in all of the set regions of concern.

As described above, the processed element data generated in the multiline processing is equal element data in a case where the focus points are linked at a large number of points on a sound ray to be transmitted by eliminating the influence of the ghost. That is, the processed element data generated in the multiline processing refers to element data obtained by the transmission of the ultrasonic waves at multiple virtual focus points.

Therefore, according to the present invention which performs the determination of the sound velocities using the processed element data, even with the transmission of ultrasonic waves at one focus point on one sound ray, it is possible to determine the sound velocity with high precision equal to or higher than in a case where the transmission of the ultrasonic waves is performed at many focus points on one sound ray.

On the other hand, as can be understood from the calculation method of the delay time described above, the processing of the element data in the multiline processing is performed regarding the focus points as ideal point sound sources. However, the focus points of the actual ultrasonic beam have a limited size and are not exactly point sound sources. Therefore, the premise of the point sound sources is lost in the vicinity of the focus points in some cases and there are also cases where the precision of the superimposition is decreased. When using the processed element data in this manner, conversely, there are also cases where it is not possible to determine the sound velocity with high precision.

On the other hand, in the present invention, it is determined whether or not the region of concern is in the vicinity of the focus point. Then, the sound velocity is determined using the normal element data on which the multiline processing is not performed when the region of concern is in the vicinity of the focus points and the sound velocity is determined using the processed element data obtained by the multiline processing when the region of concern is not in the vicinity of the focus points.

By the present invention having such a configuration, in a state where the focus points are matched in the entire region of the image, it is possible to determine the sound velocity even for the transmission of ultrasonic waves at one focus point for one sound ray, that is, it is possible to determine the sound velocity with high precision in the entire region of the image (the target inspection region). Moreover, since it is possible to determine the sound velocity with high precision in the transmission of ultrasonic waves at one focus point for one sound ray, it is also possible to prevent a decrease in the frame rate which accompanies the determination of the sound velocity (the updating of the sound velocity).

In the present invention, in a case where the precision of the determined ambient sound velocity is determined and the precision does not satisfy a predetermined precision (in a case of an unsatisfactory sound velocity), the ambient sound velocity may be re-determined as necessary.

The precision determining method of the ambient sound velocity is not particularly limited and it is possible to use various known determining methods.

As an example, there is a method where, after dividing an image into predetermined regions formed of a plurality of regions of concern and calculating the standard deviation of the ambient sound velocity in the predetermined regions, the region of concern of the predetermined region is determined as the unsatisfactory sound velocity in a case where the standard deviation does not satisfy a threshold set in advance. Here, examples of the division of the image at this time, that is, the predetermined regions, include a square grid shape if the probe is a linear type and a fan shaped grid shape if the probe is a convex type.

In addition, it is also possible to use a method where in a similar predetermined region, in a case where the maximum value and the minimum value of the ambient sound velocity are detected and the difference therebetween exceeds a predetermined threshold, the sound velocity is determined to be unsatisfactory for the region of concern of the predetermined region. In addition, it is also possible to use a method where, in a similar predetermined region, in a case where the average value of the ambient sound velocity is calculated and the average value is outside a predetermined range, the sound velocity is determined to be unsatisfactory for the region of concern of the predetermined region. In addition, it is also possible to use a method where, in a similar predetermined region, in a case where the frequency distribution of the ambient sound velocity is calculated and the variation in the distribution exceeds a predetermined threshold, the sound velocity is determined to be unsatisfactory for the region of concern of the predetermined region.

Alternatively, it is also possible to use a method where, in a similar predetermined region, the average value of the ambient sound velocity is calculated and, for a region of concern where the difference between the average values exceeds a predetermined threshold, the sound velocity is determined to be unsatisfactory.

Furthermore, for the ambient sound velocity of the predetermined region, a satisfactory sound velocity and an satisfactory sound velocity may be determined using an integrated value, a squared integral value, a peak value, a contrast, a frequency spectrum integration, a frequency spectrum integral value or a squared integral value normalized by a maximum value or a DC component, an autocorrelation value, or the like.

With regard to the region of concern where the sound velocity is unsatisfactory, the ambient sound velocity may be re-determined using the processed element data obtained by performing the same multiline processing after performing the transmission of the ultrasonic waves with the focus point changed. Alternatively, the ambient sound velocity may be re-determined by performing transmission of the ultrasonic waves where the focus points are matched in the region of concern where the sound velocity is unsatisfactory and using the normal element data on which the multiline processing is not performed.

In a case where the precision of the determined ambient sound velocity is determined, it is preferable that the redetermination of the sound velocity and the precision determination be repeated until the sound velocities of all of the regions of concern are a predetermined precision or better (until the sound velocity is satisfactory).

The ultrasound diagnostic apparatus, the sound velocity determining method, and the program of the present invention have been described above; however, the present invention is not limited to the examples described above and various improvements or modifications may be made within a range which does not depart from the gist of the present invention as a matter of course.

For example, in the ultrasound diagnostic apparatus 10 of the example in the diagram, the image generator 24 generates an ultrasound image using processed element data generated by a multiline processing as a preferable embodiment; however, the present invention is not limited thereto.

That is, when the ultrasound diagnostic apparatus of the present invention performs the sound velocity determination of the ultrasonic waves in the subject using the normal element data in the vicinity of the focus points and performs the sound velocity determination using the processed element data generated using the multiline processing in the other regions, the generation of the ultrasound image may be performed using the normal element data.

In addition, in order to perform the multiline process to be described below without having the element data storage 20 which stores the element data for one image, the transmission and reception of the ultrasonic waves may be performed every time or a necessary number of times corresponding to one element-of-concern.

What is claimed is:

1. An ultrasound diagnostic apparatus, which inspects an inspection object sing an ultrasonic beam, comprising:
    a probe in which a plurality of elements are arranged, which transmit the ultrasonic beam, receive ultrasonic echoes reflected by the inspection object, and output an analog element signal according to the received ultrasonic echoes;
    a transmitter configured to make the probe perform transmission of the ultrasonic beam a plurality of times so as to form predetermined transmission focus points using the plurality of elements; a receiver configured to receive an analog element signal output by the plurality of elements corresponding to the transmission of the ultrasonic beam toward each of the transmission focus points, and carrying out a predetermined process;
    an analog-to-digital converter configured to analog-to-digital convert the analog element signal processed by the receiver into first element data which is a digital element signal before performing phasing addition;
    a data processor configured to generate second element data which is a digital element signal before performing phasing addition corresponding to any one of a plurality of first element data;
    a sound velocity determiner configured to determine a sound velocity of ultrasonic waves in the inspection object using the first element data or the second element data; and
    a position determiner configured to determine whether or not a position at which the sound velocity determiner determines the sound velocity is within a predetermined distance from a position of one of the transmission focus points;
    an image former configured to form an ultrasound image; and
    a display configured to display an ultrasound image formed by the image former,
    wherein the sound velocity determiner determines the sound velocity using the first element data in a case where the sound velocity determining position is within the predetermined distance from the one of the transmission focus points according to determination results by the position determiner and determines the sound velocity using the second element data in a case where the sound velocity determining position is not within the predetermined distance from the one of the transmission focus points,
    wherein the image former forms the ultrasound image by performing phasing addition for forming the ultrasound image using at least one of the first element data and the second element data using the sound velocity determined by the sound velocity determiner, and
    wherein the data processor generates the second element data corresponding to the first element data with one element of interest being a center element being rebuilt by superimposing the plurality of first element data each with a different center element on the first element data with the element of interest being the center element according to a positional difference between center elements, a reception time at which the elements received the ultrasonic echoes and positions of the elements.

2. The ultrasound diagnostic apparatus according to claim 1, wherein the transmitter makes the probe perform transmission of the ultrasonic beam a plurality of times, changing at least one of a center element and a transmission direction of the ultrasonic beam.

3. The ultrasound diagnostic apparatus according to claim 2, wherein the data processor generates the second element data using at least one of a plurality of the first element data obtained by transmission of the ultrasonic beam where the center elements are different to each other and a plurality of the first element data obtained by transmission of the ultrasonic beam where the transmission directions are different to each other.

4. The ultrasound diagnostic apparatus according to claim 1, wherein the data processor generates the second element data from the plurality of first element data obtained by transmission of the ultrasonic beam where transmission regions overlap.

5. The ultrasound diagnostic apparatus according to claim 1, wherein a measurement region in a subject is divided into a plurality of regions and the sound velocity is determined for each divided region.

6. The ultrasound diagnostic apparatus according to claim 1, wherein the transmitter performs the transmission of the ultrasonic beam for one sound ray at only one of the transmission focus points when determining the sound velocity.

7. The ultrasound diagnostic apparatus according to claim 1, further comprising: an element data storage unit which stores all of the first element data corresponding to at least one ultrasound image.

8. The ultrasound diagnostic apparatus according to claim 1, wherein an ultrasound image is formed using the second element data.

9. An ultrasound image forming method in ultrasound diagnosis using a probe in which a plurality of elements are arranged, which transmit an ultrasonic beam, receive ultrasonic echoes reflected by an inspection object, and output an analog element signal according to the received ultrasonic echoes, the method comprising:

making the probe perform transmission of the ultrasonic beam a plurality of times so as to form predetermined transmission focus points using the plurality of elements when determining a sound velocity of the ultrasonic waves inside an inspection object;

analog-to-digital converting an analog element signal output by the plurality of elements into first element data which is a digital element signal before performing phasing addition corresponding to the individual transmission of the ultrasonic beam corresponding to each of the transmission focus points;

generating, using a plurality of first element data, second element data which is a digital element signal before performing phasing addition corresponding to any one of the plurality of first element data;

determining whether or not a position for determining the sound velocity of the ultrasonic waves in the inspection object is within a predetermined distance from one of the transmission focus points;

determining the sound velocity using the first element data in a case where the position for determining the sound velocity is within the predetermined distance from one of the transmission focus points and determining the sound velocity using the second element data in a case where the position for determining the sound velocity is not within the predetermined distance from one of the transmission focus points; and forming the ultrasound image by performing phasing addition for forming the ultrasound image using at least one of the first element data and the second element data using the sound velocity determined, wherein the second element data is element data corresponding to the first element data with one element of interest being a center element being rebuilt and is generated by superimposing the plurality of first element data each with a different center element on the first element data with the element of interest being the center element according to a positional difference between center elements, a reception time at which the elements received the ultrasonic echoes and positions of the elements.

10. The ultrasound image forming method according to claim 9, wherein the probe performs transmission of the ultrasonic beam a plurality of times, changing at least one of a center element and a transmission direction of the ultrasonic beam.

11. The ultrasound image forming method according to claim 10, wherein the second element data is generated using either one of or both of the plurality of first element data obtained by transmission of the ultrasonic beam where the center elements are different to each other and the plurality of first element data obtained by transmission of the ultrasonic beam where the transmission directions are different to each other.

12. The ultrasound image forming method according to claim 9, wherein the second element data is generated from the plurality of first element data obtained by transmission of the ultrasonic beam where transmission regions overlap.

13. The ultrasound image forming method according to claim 9, wherein a measurement region in a subject is divided into a plurality of regions and the sound velocity is determined for each divided region.

14. The ultrasound image forming method according to claim 9, wherein the transmission of the ultrasonic beam for one sound ray is performed at only one of the transmission focus points.

15. A non-transitory computer-readable recording medium which records a program making a computer execute the steps of:

making a probe in which a plurality of elements are arranged, which transmit the ultrasonic beam, receive ultrasonic echoes reflected by an inspection object, and output an analog element signal according to the received ultrasonic echoes, perform transmission of an ultrasonic beam a plurality of times so as to form predetermined transmission focus points using the plurality of elements;

analog-to-digital converting an analog element signal output by the elements into first element data which is a digital element signal before performing phasing addition corresponding to the individual transmission of the ultrasonic beam;

generating, using a plurality of first element data, second element data which is a digital element signal before performing phasing addition corresponding to any one of the plurality of first element data;

determining whether or not a position for determining the sound velocity in the inspection object is within a predetermined distance from one of the transmission focus points; and determining the sound velocity using the first element data in a case where the position for determining the sound velocity is within the predetermined distance from one of the transmission focus points, and determining the sound velocity using the second element data in a case where the position for determining the sound velocity is not within the predetermined distance from one of the transmission focus points; and forming the ultrasound image by performing phasing addition for forming the ultrasound image using at least one of the first element data and the second element data using the sound velocity determined, wherein the step of generating the second element data generates the second element data corresponding to the first element data with an element of interest being a center element is being rebuilt by superimposing the plurality of first element data each with a different center element on the first element data with the element of interest being the center element according to a positional difference between center elements, a reception time at which the elements received the ultrasonic echoes and positions of the elements.

16. The non-transitory computer-readable recording medium according to claim 15, wherein in the step of making a probe transmit the ultrasonic beam, the probe perform transmission of the ultrasonic beam a plurality of times, changing at least one of a center element and a transmission direction of the ultrasonic beam.

17. The non-transitory computer-readable recording medium according to claim 16, wherein in the step of generating the second element data, the second element data is generated using either one of or both of a plurality of first element data obtained by transmission of the ultrasonic beam where center elements are different to each other and a plurality of first element data obtained by transmission of the ultrasonic beam where transmission directions are different to each other.

18. The non-transitory computer-readable recording medium according to claim 15, wherein in the step of generating the second element data, the second element data is generated from a plurality of first element data obtained by transmission of the ultrasonic beam where transmission regions overlap.

* * * * *